United States Patent
Schyns et al.

(10) Patent No.: US 9,631,185 B2
(45) Date of Patent: Apr. 25, 2017

(54) FUSION OF BIOACTIVE MOLECULES

(75) Inventors: Ghislain Schyns, Basel (CH); Stephane Duval, Saint-Louis (FR); Aurelie Brelin, Basel (CH)

(73) Assignee: NOVOZYMES A/S, Bagsvaerd (DK)

( * ) Notice: Subject to any disclaimer, the term of this patent is extended or adjusted under 35 U.S.C. 154(b) by 31 days.

(21) Appl. No.: 14/124,769

(22) PCT Filed: Jun. 11, 2012

(86) PCT No.: PCT/EP2012/061003
§ 371 (c)(1),
(2), (4) Date: Aug. 14, 2014

(87) PCT Pub. No.: WO2012/168473
PCT Pub. Date: Dec. 13, 2012

(65) Prior Publication Data
US 2014/0356478 A1    Dec. 4, 2014

(30) Foreign Application Priority Data

Jun. 9, 2011 (EP) ................................. 11169295

(51) Int. Cl.
| | | |
|---|---|---|
| *C12N 9/16* | (2006.01) | |
| *C07K 14/32* | (2006.01) | |
| *C07K 14/335* | (2006.01) | |
| *A23K 20/174* | (2016.01) | |
| *A23K 20/147* | (2016.01) | |
| *A23K 20/189* | (2016.01) | |
| *A23K 20/20* | (2016.01) | |
| *A23K 50/75* | (2016.01) | |
| *A23K 50/30* | (2016.01) | |
| *A23K 50/80* | (2016.01) | |
| *A23L 33/18* | (2016.01) | |

(52) U.S. Cl.
CPC .............. *C12N 9/16* (2013.01); *A23K 20/147* (2016.05); *A23K 20/174* (2016.05); *A23K 20/189* (2016.05); *A23K 20/30* (2016.05); *A23K 50/30* (2016.05); *A23K 50/75* (2016.05); *A23K 50/80* (2016.05); *A23L 33/18* (2016.08); *C07K 14/32* (2013.01); *C07K 14/335* (2013.01); *C12Y 301/03008* (2013.01); *C07K 2319/00* (2013.01); *C12Y 301/03026* (2013.01)

(58) Field of Classification Search
CPC ........................................................ C12N 9/16
See application file for complete search history.

(56) References Cited

U.S. PATENT DOCUMENTS 6,610,524 B2 * 8/2003 Rhee ............... C12Y 301/0103
435/196
7,632,668 B2 * 12/2009 Lanahan ................. A23K 1/003
435/196
2005/0112612 A1   5/2005 Klaenhammer et al.

FOREIGN PATENT DOCUMENTS

| WO | WO9009436 A1 * | 8/1990 |
| WO | 97/14802 A1 | 4/1997 |
| WO | WO 01/22806 | 4/2001 |
| WO | WO 03/057248 | 7/2003 |

OTHER PUBLICATIONS

Hartford et al., "Matrix-binding proteins of *Staphylococcus aureus*: functional analysis of mutant and hybrid molecules", Microbiology (1999), 145, 2497-2505.*
Roos et al., "A high-molecular-mass cell-surface protein from Lactobacillus reuteri 1063 adheres to mucus components", Microbiology (2002), 148, 433-442.*
Nilsson et al., "Immobilization and purification of enzymes with staphylococcal protein A gene fusion vectors", The EMBO Journal, 1985, vol. 4 No. 4 pp. 1075-1080.*
Fahnestock et al., "Expression of the *Staphylococcal* Protein A Gene in Bacillus subtilis by Gene Fusions Utilizing the Promoter from a Bacillus amyloliquefaciens alpha-Amylase Gene", Journal of Bacteriology, Mar. 1986, vol. 165, No. 3, pp. 796-804.*
Potot et al., "Display of recombinant proteins on Bacillus subtilis spores, using a coat-associated enzyme as the carrier", *Applied and Environmental MicroBiology* Sep. 2010, vol. 76, No. 17, Sep. 2010, pp. 5926-5933.
Potot et al., "Bacillus subtilis spores to display functional enzymes", *New Biotechnology*, vol. 25, No. Suppl. 1, Sep. 2009, p. S97.
International Search Report for PCT/EP2012/061003, mailed Dec. 12, 2012.
Hsueh et al., J. Agric. Food Chem., vol. 58, pp. 12182-12191 (2010).
Linden et al., Arch. Microbiol., vol. 190, pp. 101-104 (2008).
Niemann et al., Cell, vol. 130, pp. 235-246 (2007).
Wright et al., Doctoral Thesis entitled "A Putative Mucin-degrading Operon and a 6-Sulfo-N-acetyl-beta-D-glucosaminidase in Prevotella strain RS2" submitted to the University of Auckland, Anaerobic Microbial Research Group, School of Biological Sciences (2003).
Zhou et al., Vaccine, vol. 24, No. 22, pp. 4830-4837 (2006).
Matsushita et al, 2001, J Biol Chem, vol. 276, No. 12, pp. 8761-8770.

* cited by examiner

*Primary Examiner* — Suzanne M Noakes
(74) *Attorney, Agent, or Firm* — Elias Lambiris

(57) ABSTRACT

Fusion-proteins containing an enzyme, preferably a feed or food enzyme, coupled to a gut surface-binding domain are presented. The fusion-proteins can be used to promote feed utilization in animals. In a particular example, a Fusion enzyme according to the invention comprising a gut-surface-binding polypeptide segment linked to a phytase show an increased resident time in the gut, which leads to an increased amount of time given to the enzyme to catalyse the corresponding reaction which finally leads to improved feed utilisation.

21 Claims, 4 Drawing Sheets

Figure 1:
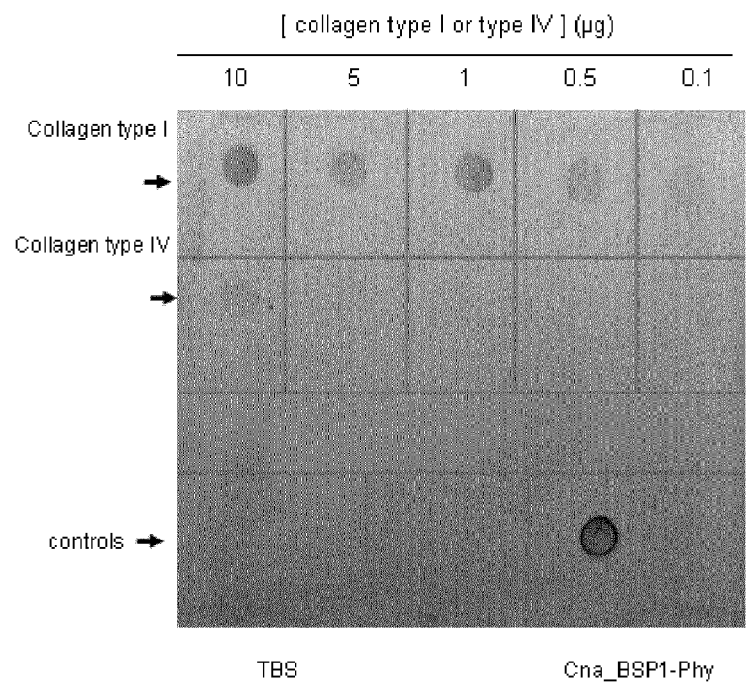

Incubation with 30 nM of Mub-phy
Detection by AB against Histag

SEQUENCE LISTING

```
<160> NUMBER OF SEQ ID NOS: 11

<210> SEQ ID NO 1
<211> LENGTH: 4829
<212> TYPE: DNA
<213> ORGANISM: Artificial Sequence
<220> FEATURE:
<223> OTHER INFORMATION: Synthetic Construct

<400> SEQUENCE: 1
cggccgccca gactgtccgc tgtgtaaaaa ataggaataa aggggggttg ttattatttt      60
actgatatgt aaaatataat ttgtataaga aaatgagagg gagaggaaat taattaaaaa     120
aggagcgatt tacatatgag ttatgcagtt tgtagaatgc aaaaagtgaa atcaggggga     180
tccagaaagg aggtgatcca atgaacacac tggcaaactg gaagaagttt ttgcttgtgg     240
cggttatcat ttgttttttg gttccaatta tgacaaaagc ggagattgcg gaagctgctg     300
tcgacgtaac gtccagtgac agccaatttt tcgatttggt aacagttaag gacgccaaag     360
gccagatagt tgacggatca aaaggaaacg aaccggcact aacaccgggg gacgaagtga     420
cactgacata tgaatggtca ttgaaaaaag acaaaaaagc agatagcgaa caggatatca     480
atgtggagtt acctaaaagc tttacatttg ataaaggtgc tgaaggtgag atcaaatctg     540
ctgatcaggt catcggcagc tatcaagtgc cggcgggcag cagcaccatg acagtaaaat     600
taacaactgc atccgcggat tctcttgatg ccaagggac cattacactg ccagctaagt     660
ttactgcaga tgtaaaagaa gatgaacata cagcagcagc cctttttcag ctaggcggag     720
gcaaaaccca gcaggtgatc attcctgtta agaaagagga gacaccagat gccgaggcgg     780
aagagccaaa aaacgactct tctgatactg cgggtgatca ggaagggaaa gatgacaaac     840
```

```
ctgcaccttc agtcagcaag gatcaaaaag aggaagaaca gcagccgtca gatgactcta    900
agagcggcga agcctctaag agtgatgatt caaaaaaagt gtcatcctca agtcaatcag    960
ctttcaaaag cttgcaaact gaagaaaaac aaatcacgca acatatttta actggcgtga   1020
cgttgacgga cgaaaacgga aagccatatg acaagggcaa tcgcgccaat acgaattctc   1080
cggtgaaaat ttcaattgat tgggctattc ctgacgattt aggaaaaacg atcaatgccg   1140
gcgataaata tgaatttgat ttgcctaaag aatttattat gcataatgac attgtgaacc   1200
gccgttaggc gccggagaca ccacctacgg gacattttct attgatacga cggacatgtg   1260
gtgatgacat taacggcga ggtaaaagaa agttctaatg caaaggcaca ttggttatca    1320
atacgcagtt caacgagaaa aaaataacgg ttcgacaaca caaaagattc catttcctgt   1380
gaatgccgat actcctgaaa acagtttat tttaaaccca atgtgagtaa aaccattgat    1440
aaatcaggtg gctggataaa ggcatcaacc ctggtaaagt aacatggacg gtcgatgtca   1500
taagaagttg gatcaagtca aaaatgccaa actcacggaa agctttccag tggcgtaatc   1560
taccgttcag ttaaagtgta tgaactcaat gtgaacattg tggttctgtc agcagaggaa   1620
atgaagtttc ttcaggctac agtgttgatt aaaaggaaat gtcacatttg acgggacaat   1680
tgattcagcc taccgccttg atacgaaacc gacattgaca atggtgcgaa gccgagtgaa   1740
ggcggaaata aacgctgaca ataaggcgg cattcagcgg agacaacctg aacccatt     1800
tgcagaagcc actgttgcag ccaagtatgg aaaaatgatc gcgaaatcat gaccggctat   1860
gatggagaat ctcaaacatt cagttgggct cttgcataca ctacggtgag aaacagatcg   1920
accaatccaa ggccagcatt aaagattctt tggaactggt gatttgcatc ttgtgaaaga   1980
ttctttgaag gttattccta tacctttggt cagaatggca gcgagcaagc gggcaggcct   2040
ttaaaggaag cgaggactac acgctgatcg ataatggaag cggatttgaa gtcaaattta   2100
taaaaacgta acgagcgctt acaaaatcac atatcaaaca aggtcaaca cggagtgatc    2160
attgataaat ctacaacata caccaatagc gttgtgaccg aacaggggat tcaaaagaag   2220
cttctggaat agccattcag caaaatctca caaaggatat tcaaacgttg attatgagaa   2280
gaagacggct gattggacga tacagttaat aaaaataaat acttgatgaa caattggact   2340
ttggatgatc atttgaaagc ggcggaatgg ttctgcttga tgaatcgttc aagcttcaag   2400
acacaacgaa caacaaaaca ttacagaaag acaaagacta cacgttaaca aaaaaacctg   2460
atcataaagg ctttactttg gcattgatcg gggattatgc aaaaacagac agtcaattta   2520
agatcactta tacgacaacg ttcaatgccg attattctaa cgaaagcgtt aagaatacag   2580
ctcagtctac atggactgat caaaacggca atgagcgcac gaataaggta tcaagcggtt   2640
ttacgccgaa taatcagacg acaaacaatg gtttcaagaa cggttcatac aacgcggttt   2700
caaaggaaat cacgtggaaa atcggcgtca attataatgg cgagccgacg aaaaaccctt   2760
atatcaaaga tgccataaca gatcctcagc aatttgtgcc gggttccgtt gtggttaaga   2820
gctatacgat caataaaaac ggctccatca cagaaggaga cgcgctggat ctgcaagttt   2880
atgatgtcga agagccttct gcaaaaaatg aacacactct gacggtacac cttaaaacag   2940
gcgattctgt accatatctg attgagttta agacatcact caaggacag gtcattgatc   3000
agaatcagta cacaaacaag gcaacctact ataatgacgg ttatgcagac cgcacactga   3060
cgggctctgt ttcagttacg aacggaggaa gcctggtttt caaaggcggc aaacaaaatg   3120
gaagctcat cgattggaac atcaatgtca actccagcca atcaacgctg atgacgtaa    3180
aagttactga cacgccggat gaaaatcaaa tactagatgc agattctttt aaagtatatc   3240
```

```
aagcaaaata tgatgaaaac ggagtggtca agacagcag cggaaatctg accgcgggag    3300
atgtcgagct tcaaaaagac aaagactaca cgttagacat caaaacggac aatacaacag    3360
gtgaacaatc gtttgtcctg aaattcatag gcagctataa gcaaattgat cgcgcctatg    3420
tgatcaaata ccggtctctg attaacatag ccggcacgag cggccatgtt aaaaataagg    3480
tgtccatttc aggaacaaat gtgaaggagg cagcagctgc tgctgcggct gcggcagcag    3540
aagaacaaaa cggcatgaag cttgaacgcg ttgtcattgt cagcagacac ggcgttcgtg    3600
cgccgacaaa attcacaccg attatgaagg atgtgacacc tgaccaatgg ccgcaatggg    3660
atgtgccgct cggctggctg acgccaagag gcggagagct tgtttctgag ctcggacaat    3720
atcagcgctt gtggtttaca agcaaaggtc tcctgaataa ccaaacgtgc ccatctccag    3780
gacaagtagc tgttatcgct gacactgatc agcggacaag aaaaacaggc gaagcatttt    3840
tggcagggct tgcgccgaaa tgccaaattc aagtacacta tcaaaagac gaagaaaaaa    3900 acgacccgct gttcaacccg gttaaaatgg gaaaatgctc gtttaacact ctaaaggtga    3960
agaatgcgat tttagagcgt gccggcggaa acattgagct ttacacacag cgctatcaat    4020
catctttccg tacgcttgaa aatgtgctga acttctctca atctgaaaca tgcaaaacaa    4080
cagaaaaatc aacaaaatgc acgcttcctg aagcgctgcc atctgagttt aaagtaacgc    4140
ctgacaatgt atcccttcct ggtgcatgga gcctttcctc aacgctgact gagattttcc    4200
tattgcagga agctcaaggc atgccgcaag tcgcctgggg ccggattacc ggcgaaaaag    4260
agtggaggga tttgctgtca cttcacaacg ctcaatttga ccttcttcag cgtacaccag    4320
aggttgcccg ctcccgtgca accccgcttc ttgatatgat tgacacagct tgctgacaa    4380 atggcacaac tgaaaaccgt tacggcatca aacttccggt ttctctattg tttattgcag    4440
ggcatgacac aaaccttgcc aacctttccg gcgcgcttga tttaaaatgg tcgctgccag    4500
gacagccgga caatacgccg cccggcgag aactcgtatt tgaaaaatgg aaacgcactt    4560
ctgacaacac tgactgggta caggtttctt tcgtttatca aacgcttcgt gacatgcgtg    4620
acatacagcc gctcagcctt gaaaagcctg ccggaaaagt agacttaaaa ttaatcgcat    4680
gtgaagagaa aaattctcaa ggtatgtgct cgctgaaatc attctctcgc ttgattaaag    4740
aaatccgcgt gcctgaatgt gctgtcacag agctggtgcc gcgcggcagc agcagcggcc    4800
accaccacca ccaccactaa taagctagc                                      4829
```

<210> SEQ ID NO 2
<211> LENGTH: 2566
<212> TYPE: DNA
<213> ORGANISM: Artificial Sequence
<220> FEATURE:
<223> OTHER INFORMATION: Synthetic construct

<400> SEQUENCE: 2

```
cggccgccca gactgtccgc tgtgtaaaaa ataggaataa aggggggttg ttattatttt      60
actgatatgt aaaatataat ttgtataaga aaatgagagg gagaggaaat taattaaaaa     120
aggagcgatt tacatatgag ttatgcagtt tgtagaatgc aaaaagtgaa atcaggggga     180
tccagaaagg aggtgatcca atgaacacac tggcaaactg aagaagtttt tgcttgtgg     240 cggttatcat ttgtttttg gttccaatta tgacaaaagc ggagattgcg gaagctgctg     300
tcgaccgaga tatttcatca acgaatgtta cagatttaac tgtatcaccg tctaagatag     360
aagatggtgg taaaacgaca gtaaaaatga cgttcgacga taaaaatgga aaaatacaaa     420
```

-continued

```
atggtgacat gattaaagtg gcatggccga caagcggtac agtaaagata gagggttata    480
gtaaaacagt accattaact gttaaaggtg aacaggtggg tcaagcagtt attacaccag    540
acggtgcaac aattacattc aatgataaag tagaaaaatt aagtgatgtt tcgggatttg    600
cagaatttga agtacaagga agaaatttaa cgcaaacaaa tacttcagat gacaaagtag    660
ctacgataac atctgggaat aaatcaacga atgttacggt tcataaaagt gaagcgggaa    720
caagtagtgt tttctattat aaaacgggag atatgctacc agaagatacg acacatgtac    780
gatggttttt aaatattaac aatgaaaaaa gttatgtatc gaaagatatt actataaagg    840
atcagattca aggtggacag cagttagatt taagcacatt aaacattaat gtgcaggta    900 cacatagcaa ttattatagt ggacaaagtg caattactga ttttgaaaaa gcctttccag    960
gttctaaaat aactgttgat aatacgaaga acacaattga tgtaacaatt ccacaaggct   1020
atgggtcata atagttttt tcaattaact acaaaaccaa aattacgaat gaacagcaaa   1080
aagagtttgt taataattca caagcttggt atcaagagca tggtaaggaa gaagtgaacg   1140
ggaaatcatt taatcatact gtgcacaata ttaatgctaa tgccggtatt gaaggtactg   1200
taaaaggtga attaaaagtt ttaaaacagg ataaagatac caaggctgca gcagctgctg   1260
ctgcggctgc ggcagcagaa gaacaaaacg gcatgaagct tgaacgcgtt gtcattgtca   1320
gcagacacgg cgttcgtgcg ccgacaaaat tcacaccgat tatgaaggat gtgacacctg   1380
accaatggcc gcaatgggat gtgccgctcg gctggctgac gccaagaggc ggagagcttg   1440
tttctgagct cggacaatat cagcgcttgt ggtttacaag caaaggtctc ctgaataacc   1500
aaacgtgccc atctccagga caagtagctg ttatcgctga cactgatcag cggacaagaa   1560
aaacaggcga agcatttttg gcagggcttg cgccgaaatg ccaaattcaa gtacactatc   1620
aaaaagacga agaaaaaaac gacccgctgt tcaacccggt taaatgggaa aaatgctcgt   1680
ttaacactct aaaggtgaag aatgcgattt tagagcgtgc cggcggaaac attgagcttt   1740
acacacagcg ctatcaatca tctttccgta cgcttgaaaa tgtgctgaac ttctctcaat   1800
ctgaaacatg caaaacaaca gaaaaatcaa caaaatgcac gcttcctgaa gcgctgccat   1860
ctgagtttaa agtaacgcct gacaatgtat cccttcctgg tgcatggagc ctttcctcaa   1920
cgctgactga gattttccta ttgcaggaag ctcaaggcat gccgcaagtc gcctggggcc   1980
ggattaccgg cgaaaagag tggagggatt tgctgtcact tcacaacgct caatttgacc   2040
ttcttcagcg tacaccagag gttgcccgct cccgtgcaac cccgcttctt gatatgattg   2100
acacagcttt gctgacaaat ggcacaactg aaaaccgtta cggcatcaaa cttccggttt   2160
ctctattgtt tattgcaggg catgacacaa accttgccaa cctttccggc gcgcttgatt   2220
taaaatggtc gctgccagga cagccggaca atacgccgcc cggcggagaa ctcgtatttg   2280
aaaaatggaa acgcacttct gacaacactg actgggtaca ggtttctttc gtttatcaaa   2340
cgcttcgtga catgcgtgac atacagccgc tcagccttga aaagcctgcc ggaaaagtag   2400
acttaaaatt aatcgcatgt gaagagaaaa attctcaagg tatgtgctcg ctgaaatcat   2460
tctctcgctt gattaaagaa atccgcgtgc ctgaatgtgc tgtcacagag ctggtgccgc   2520
gcggcagcag cagcggccac caccaccaca ccactaataa gctagc         2566
```

<210> SEQ ID NO 3
<211> LENGTH: 4161
<212> TYPE: DNA
<213> ORGANISM: Artificial Sequence
<220> FEATURE:
<223> OTHER INFORMATION: Synthetic construct

<400> SEQUENCE: 3

```
cggccgccca gactgtccgc tgtgtaaaaa ataggaataa agggggggttg ttattatttt      60
actgatatgt aaatataat ttgtataaga aatgagagg gagaggaaat taattaaaaa        120
aggagcgatt tacatatgag ttatgcagtt tgtagaatgc aaaaagtgaa atcagggga       180
tccagaaagg aggtgatcca atgaacacac tggcaaactg gaagaagttt tgcttgtgg      240
cggttatcat ttgttttttg gttccaatta tgacaaaagc ggagattgcg gaagctgctg     300
tcgacgtgcg catcgcacca cgcggcagga tagagctgca aaaggaatcg tcgaacgcat     360
caattaccgg cgggaatgca tgctattccc tacaaggagc cgaattcgaa gtgcgggacg     420
cctcgggcaa tcatgccacg acgctcgtta ccgacgaacg gggatacgca cgttcgggcg     480
atctgctctg cggcacgtac accgtacggg aaacgaaggc gcccagggga tacgcactga     540
gcggaaggga gtttcgcgta accgttacgc ccaacaccac cacacgcgta gcggaacag      600
gaggcgtgat taccgacgaa ccattgggaa accccatcga cctgcttctg cgcaaaacgg     660
accccccaaac gggcagccat ccgcaaggcg caggctcctt ggcgggggca cgtttcaccg    720
tgcgctatta cgatggctac tacgaccagg gaaatcttcc atccaccgcc atccgatcct     780
ggacgttcga aaccgacgaa cgaggagaag ttcatttcag cgactcatac ctgaagcaag     840
gcgacgcgct ttatcgcaac gccaagaagc aacccatcgt gccctgggc accataacca     900
tccaagaggt gcaggctcct gcggggtacg cactcgacga tggcgcggga catgccacac    960
cacttcacgt cgtgcgcatc accagcgaca acacgaatgc aacatcgacc gatatcgcat   1020
gctacgcccc attcgaccaa cccgacagcg tgcaacgggg cgatttcagg ctcgtgaaaa   1080
aggtcgcatc cgaagcgggc atcgacgagc tggcgacagg agttcaattc caaatcatca   1140
acgagaacgg ccacgacgtt gcctcaccag agcccggcaa tgccctggtg aaaaaaggcg   1200
atgccgtctg caccatcacc gtcgatgcaa acggcctggc atccacgcgc aatgaagccg   1260
ccaacggctg ggccacgcca gcaagctggg ctggggcact cgcgtacgga acgtaccgca   1320
ttcacgaagt cattcccagc gaagtacagc gcgcattcgg cgaagcgcac gcaggggcaa   1380
ccatcgccac cgtgcccgac tggcgcatca cgataggcgc caacaggcaa tacgacgcgc   1440
ccgcactcgt caccgacacc gtgccccaat cgcccttgaa ggtggtgaag atcgacggcg   1500
aaacaggcaa gcccattccc ctaccctgtt cgtttcagct ctacgaccag agtggatgcc   1560
tcgttaccta cgaagcgcat taccccgaac caaccaccat ggacacgtgg accacaaatg   1620
actctggaga ggcaacgctg cccatgatgc tccacgacgg cacgtatacg ctgaaggaaa   1680
tacaggcgcc cgcaggctac atcctcgacc ccgaccccgt gcccttcacc gtggacagca   1740
cgtcgcgcac ctgggacaac cccctggtaa tcaccattgc gaaccaaccg gcaaggggaa   1800
cgattgccct ttcgaagagc gacgacgtaa cgggtacggg catcgccggg gcgcaataca   1860
acatatgcgc cgcaagcgac atagcaacgc ccgacggcac catacgcgct catgaaggcg   1920
atatagtggc ccagcttaca tgcggcgaag acggtaccgc acattcagac gaactctacc   1980
tggggtcata tcggttctac gaaaccaaag ccccgaacgg atacgcactc gaccccgagg   2040
agcacccgt agagctcacg aatgagggcc agcacgaaac cacaacggtc gccccgcag    2100
caaccaccga cgaacccacc tcattgcgca tcctgaaaac ctgctcggaa acggacaagc   2160
cacttgcagg agcaacattc tcgattgcaa gcgaggacgc aaccacgag ccaatgcaac    2220
tggaaacaga tgctaacggc gtggcctaca tcgaacacct ggggcatggc tcgtattgca   2280
```

| | | | | |
|---|---|---|---|---|
| tacgggaaac | gaaagcccca | cccggttggc | tcataagcga | ggatgccgcg cagggaacgt | 2340 |
| gcttcaccgt | aaacgaccag | ggattcattt | gcatggaagg | ggccagcgaa ttagcaagcg | 2400 |
| aggtcacgct | caacgtggaa | aacgagccaa | aaccacccga | agcgcccatt ccaagggaac | 2460 |
| tcccaaagcc | agcccacgct | tccccaccta | cgcatgacaa | tgcggcagga gcggtatgcg | 2520 |
| ccatcgtcgc | atgcatgatc | atgacgcttg | ccgtggcacg | tgccgcccaa cgcgccgcgc | 2580 |
| gaagagaccc | caagccgaag | caaacgcgcc | tacggaggaa | agcagcagct gctgctgcgg | 2640 |
| ctgcggcagc | agcggcaaat | cttaatggga | cgctgatgca | gtattttgaa tggtacatgc | 2700 |
| ccaatgacgg | ccaacattgg | aagcgttttgc | aaaacgactc | ggcatatttg gctgaacacg | 2760 |
| gtattactgc | cgtctggatt | cccccggcat | ataagggaac | gagccaagcg gatgtgggct | 2820 |
| acggtgctta | cgacctttat | gatttagggg | agtttcatca | aaaagggacg gttcggacaa | 2880 |
| agtacggcac | aaaaggagag | ctgcaatctg | cgatcaaaag | tcttcattcc cgcgacatta | 2940 |
| acgtttacgg | ggatgtggtc | atcaaccaca | aaggcggcgc | tgatgcgacc gaagatgtaa | 3000 |
| ccgcggttga | agtcgatccc | gctgaccgca | accgcgtaat | tcaggagaaa cacctaatta | 3060 |
| aagcctggac | acattttcat | tttccggggc | gcggcagcac | atacagcgat tttaaatggc | 3120 |
| attggtacca | ttttgacgga | accgattggg | acgagtcccg | aaagctgaac cgcatctata | 3180 |
| agtttcaagg | aaaggcttgg | gattgggaag | tttccaatga | aaacggcaac tatgattatt | 3240 |
| tgatgtatgc | cgacatcgat | tatgaccatc | ctgatgtcgc | agcagaaatt aagagatggg | 3300 |
| gcacttggta | tgccaatgaa | ctgcaattgg | acggtttccg | tcttgatgct gtcaaacaca | 3360 |
| ttaaattttc | ttttttgcgg | gattgggtta | atcatgtcag | ggaaaaaacg gggaaggaaa | 3420 |
| tgtttacggt | agctgaatat | tggcagaatg | acttgggcgc | gctggaaaac tatttgaaca | 3480 |
| aaacaaattt | taatcattca | gtgtttgacg | tgccgcttca | ttatcagttc catgctgcat | 3540 |
| cgacacaggg | aggcggctat | gatatgagga | aattgctgaa | cggtacggtc gtttccaagc | 3600 |
| atccgttgaa | atcggttaca | tttgtcgata | accatgatac | acagccgggg caatcgcttg | 3660 |
| agtcgactgt | ccaaacatgg | tttaagccgc | ttgcttacgc | ttttattctc acaagggaat | 3720 |
| ctggataccc | tcaggttttc | tacggggata | tgtacgggac | gaaaggagac tcccagcgcg | 3780 |
| aaattcctgc | cttgaaacac | aaaattgaac | cgatcttaaa | agcgagaaaa cagtatgcgt | 3840 |
| acggagcaca | gcatgattat | ttcgaccacc | atgacattgt | cggctggaca agggaaggcg | 3900 |
| acagctcggt | tgcaaattca | ggtttggcgg | cattaataac | agacggaccc ggtggggcaa | 3960 |
| agcgaatgta | tgtcggccgg | caaaacgccg | gtgagacatg | gcatgacatt accgaaaacc | 4020 |
| gttcggagcc | ggttgtcatc | aattcggaag | gctggggaga | gtttcacgta aacggcgggt | 4080 |
| cggtttcaat | ttatgttcaa | agatagtggt | gccgcgcggc | agcagcagcg gccaccacca | 4140 |
| ccacaccact | aataagctag | c | | | 4161 |

<210> SEQ ID NO 4
<211> LENGTH: 2269
<212> TYPE: DNA
<213> ORGANISM: Artificial Sequence
<220> FEATURE:
<223> OTHER INFORMATION: Synthetic construct

<400> SEQUENCE: 4

| | | | | |
|---|---|---|---|---|
| cggccgccca | gactgtccgc | tgtgtaaaaa | ataggaataa | aggggggttg ttattatttt | 60 |
| actgatatgt | aaaatataat | ttgtataaga | aaatgagagg | gagaggaaat taattaaaaa | 120 |
| aggagcgatt | tacatatgag | ttatgcagtt | tgtagaatgc | aaaaagtgaa atcaggggga | 180 |

```
tccagaaagg aggtgatcca atgaacacac tggcaaactg gaagaagttt tgcttgtgg      240
cggttatcat ttgtttttg gttccaatta tgacaaaagc ggagattgcg gaagctgctg      300
tcgacgaaat aaaggatctt tcagaaaata aacttccagt tatatatatg catgtaccta     360
aatccggagc cttaaatcaa aaagttgttt tctatggaaa aggaacatat gacccagatg     420
gatctatcgc aggatatcaa tgggactttg gtgatggaag tgattttagc agtgaacaaa     480
acccaagcca tgtatatact aaaaaaggtg aatatactgt aacattaaga gtaatggata     540
gtagtggaca aatgagtgaa aaaactatga agattaagat tacacatccg gtatatccaa     600
taggcactga aaaagaacca aataacagta agaaactgc aagtggtcca atagtaccag      660
gtatacctgt tagtggaacc atagaaaata caagtgatca agattatttc tattttgatg     720
ttataacacc aggagaagta aaaatagata taaataaatt agggtacgga ggagctactt     780
gggtagtata tgatgaaaat aataatgcag tatcttatgc cactgatgat gggcaaaatt     840
taagtggaaa gtttaaggca gataaaccag gtagatatta catccatctt tacatgttta     900
atggtagtta tatgccatat agaattaata tagaaggttc agtaggaaga gcagcagctg     960
ctgctgcggc tgcggcagca gaagaacaaa acggcatgaa gcttaacgc gttgtcattg     1020
tcagcagaca cggcgttcgt gcgccgacaa aattcacacc gattatgaag gatgtgacac    1080
ctgaccaatg gccgcaatgg gatgtgccgc tcggctggct gacgccaaga ggcggagagc    1140
ttgtttctga gctcggacaa tatcagcgct tgtggtttac aagcaaaggt ctcctgaata    1200
accaaacgtg cccatctcca ggacaagtag ctgttatcgc tgacactgat cagcggacaa    1260
gaaaaacagg cgaagcattt ttggcagggc ttgcgccgaa atgccaaatt caagtacact    1320
atcaaaaaga cgaagaaaaa aacgacccgc tgttcaaccc ggttaaaatg ggaaaatgct    1380
cgtttaacac tctaaaggtg aagaatgcga ttttagagcg tgccggcgga aacattgagc    1440
tttacacaca gcgctatcaa tcatctttcc gtacgcttga aaatgtgctg aacttctctc    1500
aatctgaaac atgcaaaaca acagaaaaat caacaaaatg cacgcttcct gaagcgctgc    1560
catctgagtt taaagtaacg cctgacaatg tatcccttcc tggtgcatgg agcctttcct    1620
caacgctgac tgagatttc ctattgcagg aagctcaagg catgccgcaa gtcgcctggg     1680
gccggattac cggcgaaaaa gagtggaggg atttgctgtc acttcacaac gctcaatttg    1740
accttcttca gcgtacacca gaggttgccc gctcccgtgc aaccccgctt cttgatatga    1800
ttgacacagc tttgctgaca aatggcacaa ctgaaaaccg ttacggcatc aaacttccgg    1860
tttctctatt gtttattgca gggcatgaca caaaccttgc caacctttcc ggcgcgcttg    1920
atttaaaatg gtcgctgcca ggacagccgg acaatacgcc gcccggcgga gaactcgtat    1980
ttgaaaaatg gaaacgcact tctgacaaca ctgactgggt acaggtttct ttcgtttatc    2040
aaacgcttcg tgacatgcgt gacatacagc cgctcagcct tgaaaagcct gccggaaaag    2100
tagacttaaa attaatcgca tgtgaagaga aaattctca ggtatgtgc tcgctgaaat      2160
cattctctcg cttgattaaa gaaatccgcg tgcctgaatg tgctgtcaca gagctggtgc    2220
cgcgcggcag cagcagcggc caccaccacc acaccactaa taagctagc                2269
```

<210> SEQ ID NO 5
<211> LENGTH: 2790
<212> TYPE: DNA
<213> ORGANISM: Artificial Sequence
<220> FEATURE:
<223> OTHER INFORMATION: Synthetic construct

```
<400> SEQUENCE: 5
cggccgccca gactgtccgc tgtgtaaaaa ataggaataa aggggggttg ttattatttt      60
actgatatgt aaaatataat ttgtataaga aaatgagagg gagaggaaat taattaaaaa     120
aggagcgatt tacatatgag ttatgcagtt tgtagaatgc aaaaagtgaa atcagggga      180 tccagaaagg aggtgatcca atgaacacac tggcaaactg aagaagtttt ttgcttgtgg     240
cggttatcat ttgttttttg gttccaatta tgacaaaagc ggagattgcg gaagctgctg     300
tcgacgttgt ttatgtagct gacacgcaag aagctgccat cagcttctat gacgagacag     360
accacaagcc actgaatgac caaacgattc agcagactgg caagactggt gaaaagatca     420
gccataccga agctaatcaa acactggcta agctgggaaa gcaaggctat gttgtagacc     480
agaatacttt tgctgatgat gcaacgtatg acaacgatac gcaagcacca caagagttta     540
cgatctacct caagcatgat acgacccata ctgacgcaac tagctcaaag gcagatcaaa     600
agaccgtcag cgaaacgatt cactacgtct acaaagatgg ggtcaacgct aataagccgg     660
tagctgatga cgctaataca acggttacct tcaaacgcgg ctacacgact gacaaagtta     720
cgggaaagat tgtttcctat gatccttgga cggttgatgg caagcaagcc gacagcaaga     780
cgtttgatgc cgtcaagagt ccagtcattg ctggttacac ggccgatcaa gcagaagttg     840
ccgctcaaac ggtaacgcca gattcccaaa atattaacaa gacagtttac tataccgctg     900
acacgcaaga agctgccatc aacttctatg acgagacagg ccacaagctg ttagataacc     960
aaacgattca tttgactggc aagaccggtg aaaaggtaga ccggacgcaa gcggaccaga    1020
cgttggctga tctggtaaag caaggctatg ttttggataa agaaaacacg gccaaggcat    1080
tcccagctaa cgcggtatat gacaacaatg accaaacgcc acaagagttt acgatctacc    1140
tcaagcatgg tacgacccat actgacgcaa ccagctcaaa ggcagatcaa aagaccgtca    1200
gcgaaacgat tcactacgtc tacaaagatg gggtcaacgc taataagccg gtagctgatg    1260
acgctaatac aacggttacc ttcaaacgcg gctacacgac tgacaaagtt acgggaaaga    1320
ttgtttccta tgatccttgg acggttgatg gcaagcaagc cgacagcaag acgtttgatg    1380
ccgtcaagag tccagtcatt gctggttaca cggccgatca agcagaagtt gccgctcaaa    1440
cggtaacgcc agattcccaa aatattaaca agacacagct gctgctgcgg ctgcggcagc    1500
agaagaacaa aacggcatga agcttgaacg cgttgtcatt gtcagcagac acggcgttcg    1560
tgcgccgaca aaattcacac cgattatgaa ggatgtgaca cctgaccaat ggccgcaatg    1620
ggatgtgccg ctcggctggc tgacgccaag aggcggagag cttgtttctg agctcggaca    1680
atatcagcgc ttgtggttta caagcaaagg tctcctgaat aaccaaacgt gcccatctcc    1740
aggacaagta gctgttatcg ctgacactga tcagcggaca agaaaaacag gcgaagcatt    1800
tttggcaggg cttgcgccga aatgccaaat tcaagtacac tatcaaaaag acgaagaaaa    1860
aaacgacccg ctgttcaacc cggttaaaat gggaaaatgc tcgtttaaca ctctaaaggt    1920
gaagaatgcg attttagagc gtgccggcgg aaacattgag ctttacacac agcgctatca    1980
atcatctttc cgtacgcttg aaaatgtgct gaacttctct caatctgaaa catgcaaaac    2040
aacagaaaaa tcaacaaaat gcacgcttcc tgaagcgctg ccatctgagt ttaaagtaac    2100
gcctgacaat gtatcccttc ctggtgcatg gagcctttcc tcaacgctga ctgagatttt    2160
cctattgcag gaagctcaag gcatgccgca agtcgcctgg ggccggatta ccggcgaaaa    2220
agagtggagg gatttgctgt cacttcacaa cgctcaattt gaccttcttc agcgtacacc    2280
agaggttgcc cgctcccgtg caaccccgct tcttgatatg attgacacag ctttgctgac    2340
```

```
aaatggcaca actgaaaacc gttacggcat caaacttccg gtttctctat tgtttattgc    2400
agggcatgac acaaaccttg ccaacctttc cggcgcgctt gatttaaaat ggtcgctgcc    2460
aggacagccg gacaatacgc cgcccggcgg agaactcgta tttgaaaaat ggaaacgcac    2520
ttctgacaac actgactggg tacaggtttc tttcgtttat caaacgcttc gtgacatgcg    2580
tgacatacag ccgctcagcc ttgaaaagcc tgccggaaaa gtagacttaa aattaatcgc    2640
atgtgaagag aaaaattctc aaggtatgtg ctcgctgaaa tcattctctc gcttgattaa    2700
agaaatccgc gtgcctgaat gtgctgtcac agagctggtg ccgcgcggca gcagcagcgg    2760
ccaccaccac cacaccacta taagctagc                                      2790
```

<210> SEQ ID NO 6
<211> LENGTH: 2851
<212> TYPE: DNA
<213> ORGANISM: Artificial Sequence
<220> FEATURE:
<223> OTHER INFORMATION: Synthetic construct

<400> SEQUENCE: 6

```
cggccgccca gactgtccgc tgtgtaaaaa ataggaataa aggggggttg ttattatttt      60
actgatatgt aaaatataat ttgtataaga aaatgagagg gagaggaaat taattaaaaa     120
aggagcgatt tacatatgag ttatgcagtt tgtagaatgc aaaaagtgaa atcaggggga     180
tccagaaagg aggtgatcca atgaacacac tggcaaactg aagaagtttt tgcttgtgg     240 cggttatcat ttgttttttg gttccaatta tgacaaaagc ggagattgcg gaagctgctg     300
tcgacagaaa ggaggtgatc caatgaacac actggcaaac tggaagaagt ttttgcttgt     360
ggcggttatc atttgttttt tggttccaat tatgacaaaa gcggagattg cggaagctgc     420
tgtcgacggt tatgaactgt tcaaggacaa cttcccagca ggtgagaagt cgataacga     480 tgacaccaac gatcaattct acacggtaat cttcaagcac catcgtgaaa acgttgatcc     540
aaaccactcc tcggctgatg gcacgaaggg tacgaagacg ctgacggaaa cggttcacta     600
caagtacgct aatggcacca aggcggctga agatcagacg gctcaggtaa cgtttacgcg     660
gaacggtgtc ctggatgacg ttacgggtat cgtggcctgg ggcaagtgga acgaagccag     720
ccagagctac aaggctttga cttcaccaac gattgccggc tacgcgccaa gcgaagcggt     780
ggtaaagcgc agttccaaca gcgatgccga acaaggccca acgcttacgg tcatctacac     840
ggctgatgcc caaaaggttc acgttcaata cattgatggt gaaactgacc agatgctgcg     900
tcaggatgat ttggacggct acacggatga acgattcct tacagcacgg ctgaaggcat     960
caagaagttt gaaggcgacg gttatgaact gttcaaggac aacttcccag caggtgagaa    1020
gttcgataac gatgacaaga tgaccaaac ctacacggta atcttcaagc accatcgtga    1080
aaacgttgat ccaaaccact cctcggctga tggcacgaag ggtacgaaga cgctgacgga    1140
aacggttcac tacaagtacg cagatggtac caaggccgct gaagatcaga cggctcaggt    1200
aacgtttacg cggaacggtg tcctggatga cgttacgggt atcgtggcct ggggcaagtg    1260
gaacgaagcc agccagagct acaaggcttt gacttcacca acgattgccg gctacacgcc    1320
aagcgaagcg gtggtaaagc gcagttccaa cagcgatgcc gaacaaggcc caacgcttac    1380
ggtcatctac acggctgatg cccaaaaggt tcacgttcaa tacattgatg gtgaaactga    1440
ccagatgctg cgtcaggatg atttggacgg ctacacggat gaaacgattc cttacagcac    1500
ggctgaaggc atcaagaagt ttgaaggcga cgcagcagct gctgccgcgg cggcagcagc    1560
```

```
agaagaacaa aacggcatga agcttgaacg cgttgtcatt gtcagcagac acggcgttcg   1620
tgcgccgaca aaattcacac cgattatgaa ggatgtgaca cctgaccaat ggccgcaatg   1680
ggatgtgccg ctcggctggc tgacgccaag aggcggagag cttgtttctg agctcggaca   1740
atatcagcgc ttgtggttta caagcaaagg tctcctgaat aaccaaacgt gcccatctcc   1800
aggacaagta gctgttatcg ctgacactga tcagcggaca agaaaaacag gcgaagcatt   1860
tttggcaggg cttgcgccga atgccaaat tcaagtacac tatcaaaaag acgaagaaaa   1920
aaacgacccg ctgttcaacc cggttaaaat gggaaaatgc tcgtttaaca ctctaaaggt   1980
gaagaatgcg attttagagc gtgccggcgg aaacattgag ctttacacac agcgctatca   2040
atcatctttc cgtacgcttg aaaatgtgct gaacttctct caatctgaaa catgcaaaac   2100
aacagaaaaa tcaacaaaat gcacgcttcc tgaagcgctg ccatctgagt ttaaagtaac   2160
gcctgacaat gtatcccttc ctggtgcatg gagccttcc tcaacgctga ctgagatttt   2220
cctattgcag gaagctcaag gcatgccgca agtcgcctgg ggccggatta ccggcgaaaa   2280
agagtggagg gatttgctgt cacttcacaa cgctcaattt gaccttcttc agcgtacacc   2340
agaggttgcc cgctcccgtg caaccccgct tcttgatatg attgacacag ctttgctgac   2400
aaatggcaca actgaaaacc gttacggcat caaacttccg gtttctctat tgtttattgc   2460
agggcatgac acaaaccttg ccaacctttc cggcgcgctt gatttaaaat ggtcgctgcc   2520
aggacagccg gacaatacgc cgccggcgg agaactcgta tttgaaaaat ggaaacgcac   2580
ttctgacaac actgactggg tacaggtttc tttcgtttat caaacgcttc gtgacatgcg   2640
tgacatacag ccgctcagcc ttgaaaagcc tgccggaaaa gtagacttaa aattaatcgc   2700
atgtgaagag aaaaattctc aaggtatgtg ctcgctgaaa tcattctctc gcttgattaa   2760
agaaatccgc gtgcctgaat gtgctgtcac agagctggtg ccgcgcggca gcagcagcgg   2820
ccaccaccac caccaccact aataagctag g                                  2851
```

<210> SEQ ID NO 7  
<211> LENGTH: 2156  
<212> TYPE: DNA  
<213> ORGANISM: Artificial Sequence  
<220> FEATURE:  
<223> OTHER INFORMATION: Synthetic construct

<400> SEQUENCE: 7

```
cggccgccca gactgtccgc tgtgtaaaaa ataggaataa agggggggttg ttattatttt     60 actgatatgt aaaatataat ttgtataaga aaatgagagg gagaggaaat taattaaaaa    120
aggagcgatt tacatatgag ttatgcagtt tgtagaatgc aaaaagtgaa atcaggggga    180
tccagaaagg aggtgatcca atgaacacac tggcaaactg gaagaagttt ttgcttgtgg    240
cggttatcat ttgttttttg gttccaatta tgacaaaagc ggagattgcg gaagctgctg    300
tcgaccagca gacacaggcg gcaactgtgc cgaccactgt tgatgttgtg ttgcataagc    360
tgttgtttaa agatacccttg ccaactcaac aagcaaataa cgggacaaca aaacccgact    420
tttcgcaggc agatgtgccg ttaaacggtg tgacgttcac agtttatgac gtgaccgctg    480
acttttggca gcttgtctcc aaaaatgcg gtgcgattga ggtagcacaa acgacgttga    540
gtcaagatag ctatcagcct gcaagctcca gccttatcgc acaggttgtg acggctggtc    600
agggagaagc gtactttggc gatttaccac tccgacaggg gcagcatgct gcggtttatc    660
tttttaaaga aacggcggca cctaagaata ttgaagccag tcagaatctt gtggttgtca    720
tgtcaagcaa ccttcaacat gggaatcaat cacgcattga tttatttcct aagaacaaaa    780
```

```
tggtaagtcg tcacaccgat gcccccaaaa aagttccaaa gaaaatacgt caattggcag      840
cagctgctgc cgcggcggca gcagcagaag aacaaaacgg catgaagctt gaacgcgttg      900
tcattgtcag cagacacggc gttcgtgcgc cgacaaaatt cacaccgatt atgaaggatg      960
tgacacctga ccaatggccg caatgggatg tgccgctcgg ctggctgacg ccaagaggcg     1020
gagagcttgt ttctgagctc ggacaatatc agcgcttgtg gtttacaagc aaaggtctcc     1080
tgaataacca acgtgccca  tctccaggac aagtagctgt tatcgctgac actgatcagc     1140
ggacaagaaa acaggcgaa  gcattttttgg cagggcttgc gccgaaatgc caaattcaag    1200
tacactatca aaaagacgaa gaaaaaaacg acccgctgtt caacccggtt aaaatgggaa     1260
aatgctcgtt taacactcta aaggtgaaga atgcgatttt agagcgtgcc ggcggaaaca     1320
ttgagcttta cacacagcgc tatcaatcat ctttccgtac gcttgaaaat gtgctgaact     1380
tctctcaatc tgaaacatgc aaaacaacag aaaaatcaac aaaatgcacg cttcctgaag     1440
cgctgccatc tgagtttaaa gtaacgcctg acaatgtatc ccttcctggt gcatggagcc     1500
tttcctcaac gctgactgag attttcctat gcaggaagc  tcaaggcatg ccgcaagtcg     1560
cctggggccg gattaccggc gaaaaagagt ggagggattt gctgtcactt cacaacgctc     1620
aatttgacct tcttcagcgt acaccagagg ttgcccgctc ccgtgcaacc ccgcttcttg     1680
atatgattga cacagctttg ctgacaaatg gcacaactga aaaccgttac ggcatcaaac     1740
ttccggtttc tctattgttt attgcagggc atgacacaaa ccttgccaac ctttccggcg     1800
cgcttgattt aaaatggtcg ctgccaggac agccggacaa tacgccgccc ggcggagaac     1860
tcgtatttga aaaatggaaa cgcacttctg acaacactga ctgggtacag gtttctttcg     1920
tttatcaaac gcttcgtgac atgcgtgaca tacagccgct cagccttgaa aagcctgccg     1980
gaaaagtaga cttaaaatta atcgcatgtg aagagaaaaa ttctcaaggt atgtgctcgc     2040
tgaaatcatt ctctcgcttg attaaagaaa tccgcgtgcc tgaatgtgct gtcacagagc     2100
tggtgccgcg cggcagcagc agcggccacc accaccacca ccactaataa gctagc        2156
```

<210> SEQ ID NO 8
<211> LENGTH: 2389
<212> TYPE: DNA
<213> ORGANISM: Artificial Sequence
<220> FEATURE:
<223> OTHER INFORMATION: Synthetic construct

<400> SEQUENCE: 8

```
cggccgccca gactgtccgc tgtgtaaaaa ataggaataa aggggggttg ttattatttt       60
actgatatgt aaaatataat ttgtataaga aaatgagagg gagaggaaat taattaaaaa      120
aggagcgatt tacatatgag ttatgcagtt tgtagaatgc aaaaagtgaa atcaggggga     180
tccagaaagg aggtgatcca atgaacacac tggcaaactg gaagaagttt ttgcttgtgg     240
cggttatcat ttgttttttg gttccaatta tgacaaaagc ggagattgcg gaagctgctg     300
tcgactctga tgaagcggcc ttgactcatg tagacaagga caatttccta agtatttta     360 gtttgaacgg atctgcaaca tatgatgcca agacgggaat tgtaactatt acgcccaatc     420
aaaataatca agttggtaat ttttcattaa ccagtaagat tgatatgaat aaaagcttta     480
cattaactgg tcaggtaaat ctggggtcta acccgaatgg tgcggatgga attgggtttg     540
cttttcacag tggcaataca actgacgtgg gaaatgctgg tggtaattta ggtattggtg     600
gattgcaaga cgctatcggg ttcaagctag acacatggtt taatagctac caagcaccat     660
```

| | |
|---|---|
| catcagataa aaatgggagt gaaatctcat caacaaattc taatggcttt ggttggaatg | 720 |
| gtgactcagc caacgcacca tatggcacct ttgtcaagac gagtaaccaa gaaatttcga | 780 |
| ctgcgaatgg ttctaaggta cagcgatggt gggctcaaga tacaggagag tcgcaggcgt | 840 |
| taagtaaagc ggatattgat ggtaactttc atgattttgt agttaactat gatggtgcta | 900 |
| caagaacgtt aaccgttagt tatacgcaag ctagtggtaa agtattaact tggaagacga | 960 |
| ctgttgacag ttcttatcaa gcaatggcca tggttgtcag tgcatcaact ggtgcagcta | 1020 |
| aaaatttaca acaatttaag ttgactagct tcgattttca agaagcagcg gcagcagctg | 1080 |
| ctgccgcggc ggcagcagca gaagaacaaa acggcatgaa gcttgaacgc gttgtcattg | 1140 |
| tcagcagaca cggcgttcgt gcgccgacaa aattcacacc gattatgaag gatgtgacac | 1200 |
| ctgaccaatg gccgcaatgg gatgtgccgc tcggctggct gacgccaaga ggcggagagc | 1260 |
| ttgtttctga gctcggacaa tatcagcgct tgtggtttac aagcaaaggt ctcctgaata | 1320 |
| accaaacgtg cccatctcca ggacaagtag ctgttatcgc tgacactgat cagcggacaa | 1380 |
| gaaaaacagg cgaagcattt ttggcagggc ttgcgccgaa atgccaaatt caagtacact | 1440 |
| atcaaaaaga cgaagaaaaa aacgacccgc tgttcaaccc ggttaaaatg ggaaaatgct | 1500 |
| cgtttaacac tctaaaggtg aagaatgcga ttttagagcg tgccggcgga aacattgagc | 1560 |
| tttacacaca gcgctatcaa tcatcttttcc gtacgcttga aaatgtgctg aacttctctc | 1620 |
| aatctgaaac atgcaaaaca acagaaaaat caacaaaatg cacgcttcct gaagcgctgc | 1680 |
| catctgagtt taaagtaacg cctgacaatg tatcccttcc tggtgcatgg agcctttcct | 1740 |
| caacgctgac tgagattttc ctattgcagg aagctcaagg catgccgcaa gtcgcctggg | 1800 |
| gccggattac cggcgaaaaa gagtggaggg atttgctgtc acttcacaac gctcaatttg | 1860 |
| accttcttca gcgtacacca gaggttgccc gctcccgtgc aaccccgctt cttgatatga | 1920 |
| ttgacacagc tttgctgaca aatggcacaa ctgaaaaccg ttacggcatc aaacttccgg | 1980 |
| tttctctatt gttattgca gggcatgaca caaaccttgc caacctttcc ggcgcgcttg | 2040 |
| atttaaaatg gtcgctgcca ggacagccgg acaatacgcc gcccggcgga gaactcgtat | 2100 |
| ttgaaaaatg gaaacgcact tctgacaaca ctgactgggt acaggtttct ttcgtttatc | 2160 |
| aaacgcttcg tgacatgcgt gacatacagc cgctcagcct tgaaaagcct gccggaaaag | 2220 |
| tagacttaaa attaatcgca tgtgaagaga aaaattctca aggtatgtgc tcgctgaaat | 2280 |
| cattctctcg cttgattaaa gaaatccgcg tgcctgaatg tgctgtcaca gagctggtgc | 2340 |
| cgcgcggcac agcagcggcc accaccacca ccaccactaa taagctagc | 2389 |

<210> SEQ ID NO 9
<211> LENGTH: 2408
<212> TYPE: DNA
<213> ORGANISM: Artificial Sequence
<220> FEATURE:
<223> OTHER INFORMATION: Synthetic construct

<400> SEQUENCE: 9

| | |
|---|---|
| cggccgccca gactgtccgc tgtgtaaaaa ataggaataa agggggggttg ttattatttt | 60 |
| actgatatgt aaaatataat ttgtataaga aaatgagagg gagaggaaat taattaaaaa | 120 |
| aggagcgatt tacatatgag ttatgcagtt tgtagaatgc aaaaagtgaa atcaggggga | 180 |
| tccagaaagg aggtgatcca atgaacacac tggcaaactg gaagaagttt ttgcttgtgg | 240 |
| cggttatcat ttgttttttg gttccaatta tgacaaaagc ggagattgcg gaagctgctg | 300 |
| tcgacatggg tatgaaaaag aaattgagtt taggagttgc ttctgcagca ctaggattag | 360 |

```
ctttagttgg aggaggaaca tgggcagcat ttaacgacat taaatcaaag gatgctactt      420
ttgcatcagg tacgcttgat ttatctgcta aagagaattc agcgagtgtg aacttatcaa      480
atctaaagcc gggagataag ttgacaaagg atttccaatt tgaaaataac ggatcacttg      540
cgatcaaaga agttctaatg gcgcttaatt atggagattt taaagcaaac ggcggcagca      600
atacatctcc agaagatttc ctcagccagt ttgaagtgac attgttgaca gttggaaaag      660
agggcggcaa tggttacccg aaaaacatta ttttagatga tgcgaacctt aaagacttgt      720
atttgatgtc tgctaaaaat gatgcagcgg ctactgaaaa aatcaaaaaa caaattgacc      780
ctaaattctt acatgcaagc ggtaaagtca atgtagcaac aattgacggt aaaactgctc      840
ctgaatatga tggtgttcca aaaacaccaa ctgacttcga tcaggttcaa atgcaaatcc      900
aattcaaaga tgataaaaca aaagatgaaa acgggcttat ggttcaaaat aaatatcaag      960
gcaactccat taagcttcaa ttctcgttcg aagctacaca gtggaacggc ttgacaatca     1020
aaaaggacca tactgataaa gacggttatg tgaaagaaaa tgaaaaagcg cacagcgagg     1080
ataaaaatgc agcagctgct gctgcggctg cggcagcaga agaacaaaac ggcatgaagc     1140
ttgaacgcgt tgtcattgtc agcagacacg gcgttcgtgc gccgacaaaa ttcacaccga     1200
ttatgaagga tgtgacacct gaccaatggc cgcaatggga tgtgccgctc ggctggctga     1260
cgccaagagg cggagagctt gtttctgagc tcggacaata tcagcgcttg tggtttacaa     1320
gcaaaggtct cctgaataac caaacgtgcc catctccagg acaagtagct gttatcgctg     1380
acactgatca gcggacaaga aaaacaggcg aagcattttt ggcagggctt cgccgaaat      1440 gccaaattca agtacactat caaaaagacg aagaaaaaaa cgacccgctg ttcaacccgg     1500
ttaaaatggg aaaatgctcg tttaacactc taaaggtgaa gaatgcgatt ttagagcgtg     1560
ccggcggaaa cattgagctt tacacacagc gctatcaatc atctttccgt acgcttgaaa     1620
atgtgctgaa cttctctcaa tctgaaacat gcaaaacaac agaaaaatca acaaaatgca     1680
cgcttcctga agcgctgcca tctgagttta agtaacgcc tgacaatgta tcccttcctg     1740
gtgcatggag cctttcctca acgctgactg agatttttcct attgcaggaa gctcaaggca     1800
tgccgcaagt cgcctggggc cggattaccg gcgaaaaaga gtggagggat ttgctgtcac     1860
ttcacaacgc tcaatttgac cttcttcagc gtacaccaga ggttgcccgc tcccgtgcaa     1920
ccccgcttct tgatatgatt gacacagctt tgctgacaaa tggcacaact gaaaaccgtt     1980
acggcatcaa acttccggtt tctctattgt ttattgcagg gcatgacaca aaccttgcca     2040 accttttccgg cgcgcttgat ttaaaatggt cgctgccagg acagccggac aatacgccgc     2100
ccggcggaga actcgtattt gaaaaatgga acgcacttc tgacaacact gactgggtac     2160
aggtttcttt cgtttatcaa acgcttcgtg acatgcgtga catacagccg ctcagccttg     2220
aaaagcctgc cggaaaagta gacttaaaat taatcgcatg tgaagagaaa aattctcaag     2280
gtatgtgctc gctgaaatca ttctctcgct tgattaaaga aatccgcgtg cctgaatgtg     2340
ctgtcacaga gctggtgccg cgcggcagca gcagcggcca ccaccaccac caccactaat     2400
aagctagc                                                             2408
```

<210> SEQ ID NO 10
<211> LENGTH: 33
<212> TYPE: DNA
<213> ORGANISM: Artificial sequence
<220> FEATURE:
<223> OTHER INFORMATION: Synthetic construct

```
<400> SEQUENCE: 10
gcatgtcgac atgggtatga aaaagaaatt gag                           33

<210> SEQ ID NO 11
<211> LENGTH: 41
<212> TYPE: DNA
<213> ORGANISM: Artificial sequence
<220> FEATURE:
<223> OTHER INFORMATION: Synthetic construct

<400> SEQUENCE: 11
gcatcagctg ctgcattttt atcctcgctg tgcgcttttt c                  41
```

FUSION OF BIOACTIVE MOLECULES

This application is the U.S. national phase of International Application No. PCT/EP2012/061003 filed 11 Jun. 2012 which designated the U.S. and claims priority to EP patent Application No. 11169295.0 filed 9 Jun. 2011, the entire contents of each of which are hereby incorporated by reference.

The present invention relates to an innovative way of constructing polypeptides and enzymes for increasing the residence time in the gastro-intestinal tract of animals based on adaptive features of microorganisms having adhesion properties as discussed herein below.

In particular, the present invention relates to a new type of polypeptides and enzymes, for example feed enzymes, which show an improved performance in animal feed as compared to a reference polypeptide or enzyme.

BACKGROUND OF THE INVENTION

Farm animals, as for example pigs and poultry, are both animals that are routinely supplemented with feed enzymes to increase feed utilization.

Phytases for example are commonly used feed enzymes for monogastric animals to improve nutritive value of animal feed and to decrease the supplementation of phosphorous to feedstuff thus reducing the environmental pollution in areas with intensive livestock production.

As for any feed enzyme, the amount of product generated (here the phosphorous) is a function of the substrate concentration (here the phytate), the enzymatic activity, and the amount of time given to the enzyme to catalyse the reaction, it is still the need to optimize feed utilisation and enzyme activity by modifying enzyme formulation or by developing new types of enzymes.

Short Description of the Technical Background

Members of the genus *Lactobacillus* but also other bacteria, in particular members of the *Bacillus* genus, are often found in the gastrointestinal tract of birds and mammals. For bacteria to be able to colonize this open flow environment, adhesion to the mucosa is considered to be a prerequisite. The epithelial cells of the intestine are covered by a protective layer of mucus, which is a complex mixture of glycoproteins and glycolipids with the large glycoprotein mucin being the main component. Bacteria colonizing the mucosa can be found both in the mucus layer and adhering to the epithelial cells. In most cases, the adhesion has been reported to be mediated by proteins, but saccharide moieties on the cell surface of lactobacilli have also been described to interact with components of the mucosa. Summarizing the present knowledge, it is known, that the ability of microbial strains to adhere to gastrointestinal components is based on their affinity to gastrointestinal mucus or its main component mucin and to collagens that are trapped into the mucus by shedding of the enterocytes or accessible when epithelium is damaged. It also known that that natural gut bacteria (including members of the *Bacillus* genus) are able to form biofilms and to adhere to epithelial cells, persist in the gut significantly longer than bacteria not able to generate biofilms. Therefore, the self-produced extracellular biofilm matrix plays also an essential role for the ability of microbial strains to adhere to gastrointestinal components Mucus-binding proteins have been characterized mainly in *Lactobacilli*. It is known that a gene from *Lactobacillis reuteri* 1063 encodes a cell-surface protein designated Mub, that adheres to mucus components. Mub is a large multi-domain protein (357 kDa) covalently attached to the cell surface as mucin-binding domain (MucBP, Pfam06458).

Collagen-binding domains can be divided into two categories:
Cna type proteins, which archetype is the protein A from *Staphylococcus aureus* (Pfam05738), mediate bacterial adhesion to collagens
CBD domains, which are part of clostridial collagenases.

TasA is a major protein component of the biofilm produced by members of the *Bacillus* genus. TasA has been detected in association with both the EPS (extracellular polymeric substance) and spores, and is thought to be required for surface adhesion.

DESCRIPTION OF THE INVENTION

In particular, the present invention relates to gut surface-binding polypeptide segments linked to a polypeptide or enzyme, preferably a feed or food enzyme. The invention also relates to DNA encoding such a fusion protein consisting of an enzyme and a gut surface-binding polypeptide segment, nucleic acid constructs, vectors, and host cells comprising the DNA as well as methods of their production, as well as the use thereof, e.g. in animal feed and animal feed additives.

The invention also relates to a method of promoting feed digestibility in an animal comprising administering to the animal a fusion-protein according to the invention. The invention also provides a feed composition or a premix comprising such a fusion-protein.

Fusion-proteins, in particular fusion-enzymes comprising a gut-surfacebinding polypeptide segment linked to the enzyme show an increased resident time in the gut, which leads to an increased amount of time given to the enzyme to catalyse the corresponding reaction which in case of feed enzymes finally leads to improved feed utilisation.

Based on protein homology, the inventors have identified on the genome of candidate strain probiotic *Bacillus subtilis* BSP1 a collagen-binding protein that is involved into the aforementioned adhesion phenomenon. This protein is the first example of a gut surface-binding polypeptide segment described hereinafter. Another gut surface-binding polypeptide segment which can be used according to the present invention is the collagen binding domain that comes from the *Staphyloccus aureus*. It is known as Cna (ProtA).

The inventors have constructed fusion proteins containing collagen binding domains from the genes bbsp1100 and bbsp1101 of probiotic strain *B. subtilis* BSP1 or part of the cna gene from *S. aureus* which were fused to the phytase gene appA of *Citrobacter braakii*.

In some embodiments of the fusion-proteins, the collagen-binding polypeptide segment is a bacterial collagen-binding polypeptide segment. In a more specific embodiment, it is a Clostridium collagen-binding polypeptide segment.

In another embodiment of the invention, the collagen-binding polypeptide segment is a segment of a collagenase, or a bacterial collagenase, or a Clostridium collagenase. Preferably the segment is only a portion of the collagenase and the collagen-binding polypeptide segment does not have collagenase activity.

The present invention also relates to the use of TasA, or another protein from the biofilm extracellular matrix, as an indirect gut-binding peptide that comes from *Bacillus subtilis* and that targets both bacterial biofilms and spores in the gut. The sequence of TasA protein has been found to be highly conserved among the members of the *Bacillus* genus as indicated below.

| Conservation of TasA protein sequence among members of the *Bacillus* genus. | |
|---|---|
| *Bacillus* species | Identity [†] |
| *B. subtilis* sp. | 96-100% |
| *B. amyloliquefaciens* sp. | 78-98% |
| *B. atrophaeus* | 83% |
| *B. licheniformis* | 71% |
| *B. pumilus* | 63% |

[†] Results of BLASTP from the National Center for Biotechnology Information (www.ncbi.nlm.nih.gov)

The DNA sequence encoding TasA, or another protein from the biofilm extracellular matrix can be fused at the carboxy-terminal or amino-terminal part of any molecule of interest (e.g. peptide, enzyme) to be bound to biofilms and spores in the gut. The inventors have constructed a fusion protein containing biofilm binding peptide from the gene bbsp3753 of the probiotic strain *B. subtilis* BSP1 which was fused to the phytase gene appA of *Citrobacter braakii*.

The present invention also relates to gut surface-binding polypeptide segments which have at least 90% identity to gut surface-binding polypeptide segments as disclosed in the examples.

The terms "fusion protein", "fusion polypeptide" or "fusion-enzyme" may be used to refer to a single polypeptide comprising two functional segments, e.g., a gut surface-binding polypeptide segment and a enzyme, preferably a feed enzyme polypeptide segment. The fusion proteins may be any size, and the single polypeptide of the fusion protein may exist in a multimeric form in its functional state, e.g., by cysteine disulfide connection of two monomers of the single polypeptide. A polypeptide segment may be a synthetic polypeptide or a naturally occurring polypeptide. Such polypeptides may be a portion of a polypeptide or may comprise a mutation or more.

The term "gut surface binding" may be used to refer to any type of polypeptide sequence that binds to the surface of the gastrointestinal tract of birds and mammals, either directly (binding to collagens or extracellular matrices (ECM) like fibronectin, fibrinogen, laminin, etc), either indirectly through the mucus (binding to mucin) that the gastrointestinal tract secretes and the molecules that it traps after shedding of enterocytes (collagens and ECM) or through biofilms or structures produced by the microbionta and that adhere to the gut surface.

Preferred enzymes according to the invention are selected from enzymes used in the feed or food industry, also referred herein as "feed-enzymes" or "food-enzymes". Particularly useful enzymes are selected from phytase (EC 3.1.3.8 or 3.1.3.26), xylanase (EC 3.2.1.8), galactanase (EC 3.2.1.89), alpha-galactosidase (EC 3.2.1.22), protease (EC 3.4.), phospholipases, beta-glucuronidase (EC 3.2.1.31), alkaline phosphatase, amylase such as, for example, alpha-amylase (EC 3.2.1.1), beta-glucanase (EC 3.2.1.4 or EC 3.2.1.6) or cellulase. Examples of phospholipases are phospholipase A1 (EC 3.1.1.32), phospholipase A2 (EC 3.1.1.4), lysophospholipase (EC 3.1.1.5), phospholipase C (EC 3.1.4.3) or phospholipase D (EC 3.1.4.4).

The phytase of the invention may be a variant of any wildtype or variant phytase.

In the present context a phytase is a polypeptide having phytase activity, i.e. an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate.

The enzyme site at the internet (www.expasy.ch/enzyme/) is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch A. The enzyme database, 2000, Nucleic Acids Res 28:304-305. See also the handbook Enzyme Nomenclature from NC-IUBMB, 1992).

According to the enzyme site, three different types of phytases are known: a so-called 3-phytase (alternative name 1-phytase; a myo-inositol hexaphosphate 3-phosphohydrolase, EC 3.1.3.8), a so-called 4-phytase (alternative name 6-phytase, name based on 1 L-numbering system and not 1D-numbering, EC 3.1.3.26), and a so-called 5-phytase (EC 3.1.3.72). For the purposes of the present invention, all three types are included in the definition of phytase.

Examples of phytases are bacterial phytases, e.g. Gram-negative phytases, such as *E. coli, Citrobacter* and *Hafnia* phytases and variants thereof, including the phytases of the present invention. Examples of fungal expression hosts are *Pichia, Saccharomyces,* and *Aspergillus* species.

Polypeptides which can be linked to gut surface-binding segments in accordance with the present invention are antimicrobial or antifungal peptides.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus,* and *Aspergillus niger* peptides, as well as variants and fragments thereof which retain antifungal activity, as disclosed in WO 94/01459 and WO 02/090384.

Performance in Animal Feed

In a particular embodiment the fusion-phytase of the invention has an improved performance in animal as compared to a reference enzyme by increasing its residence time in the gastro-intestinal tract of the animal.

In a preferred embodiment the cross linked phytase of the invention has similar performances as compared to a reference enzyme with respect to enzyme activity. The enzyme activity can be determined in an in vitro model, by preparing feed samples composed of 30% soybean meal and 70% maize meal; pre-incubating them at 40° C. and pH 3.0 for 30 minutes followed by addition of pepsin (3000 U/g feed) and phytase; incubating the samples at 40° C. and pH 3.0 for 60 minutes followed by pH 4.0 for 30 minutes; stopping the reactions; extracting phytic acid and inositol-phosphates by addition of HCl to a final concentration of 0.5M and incubation at 40° C. for 2 hours, followed by one freeze-thaw cycle and 1 hour incubation at 40° C.; separating phytic acid and inositol-phosphates by high performance ion chromatography; determining the amount of residual phytate phosphorus (IP6-P); calculating the difference in residual IP6-P between the phytase-treated and a non-phytase-treated blank sample (this difference is degraded IP6-P); and expressing the degraded IP6-P of the phytase of the invention relative to degraded IP6-P of the reference phytase.

The fusion-phytase of the invention and the reference phytase are of course dosed in the same amount, preferably based on phytase activity units (FYT). A preferred dosage is 125 FYT/kg feed. Another preferred dosage is 250 FYT/kg feed. The phytases may be dosed in the form of purified phytases, or in the form of fermentation supernatants. Purified phytases preferably have a purity of at least 95%, as determined by SDS-PAGE.

In preferred embodiments, the degraded IP6-P value of the purified fusion-phytase of the invention, relative to the degraded IP6-P value of the reference phytase is at least 90%, 95%, 98% or at least equal. In still further preferred embodiments, the degraded IP6-P value of the purified phytase of the invention, relative to the degraded IP6-P value of the reference phytase, is at least 105%, 110%.

In a still further particular embodiment, the relative performance of the fusion-phytase of the invention may be calculated as the percentage of the phosphorous released by the phytase of the invention, relative to the amount of phosphorous released by the reference phytase.

Nucleic Acid Sequences and Constructs

The present invention also relates to nucleic acid sequences comprising a nucleic acid sequence which encodes a fusion-protein or fusion-polypeptide according to the invention, preferably a fusion-phytase.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

Nucleic Acid Constructs

A nucleic acid construct comprises a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" denotes herein a configuration in which a control sequence is placed at an appropriate position relative to the coding sequence of the polynucleotide sequence such that the control sequence directs the expression of the coding sequence of a polypeptide.

When used herein the term "coding sequence" (CDS) means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may be a DNA, cDNA, or recombinant nucleotide sequence.

Expression Vector

The term "expression" includes any step involved in the production of the polypeptide, i.e. the fusion-protein or fusion-polypeptide of the invention, including, but not limited to, transcription, post-transcriptional modification, translation, post-translational modification, and secretion.

The term "expression vector" is defined herein as a linear or circular DNA molecule that comprises a polynucleotide encoding a polypeptide of the invention, and which is operably linked to additional nucleotides that provide for its expression.

A nucleic acid sequence encoding a fusion-enzyme of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding the fusion phytase of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

Host Cells

The term "host cell", as used herein, includes any cell type which is susceptible to transformation, transfection, transduction, and the like with a nucleic acid construct comprising a polynucleotide of the present invention.

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus*, *Bacillus licheniformis*, *Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizen, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Pichia pastoris*, *Pichia methanolica*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

Methods of Production

The present invention also relates to methods for producing a fusion-polypeptide or fusion-enzyme of the present invention comprising (a) cultivating a host cell under conditions conducive for production of the fusion-polypeptide or enzyme; and (b) recovering the fusion-polypeptide or enzyme.

In the production methods of the present invention, the cells are cultivated in a nutrient medium suitable for production of the fusion-polypeptide or enzyme using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide (or enzyme) to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting fusion-polypeptide or enzyme may be recovered using methods known in the art. For example, the polypeptide or enzyme may be recovered from the nutrient medium by conventional procedures including, but not limited to, centrifugation, filtration, extraction, spray-drying, evaporation, or precipitation.

The fusion-polypeptide or enzyme of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Compositions and Uses

In still further aspects, the present invention relates to compositions comprising a fusion-polypeptide or fusion-enzyme, in particular a fusion-feed-enzyme of the present invention, as well as methods of using these.

The compositions may be prepared in accordance with methods known in the art and may be in the form of a liquid or a dry composition. For instance, the composition may be in the form of granulates or microgranulates. The fusion-enzyme to be included in the composition may be stabilized in accordance with methods known in the art.

Accordingly, preferred uses of the fusion-enzymes of the invention are in animal feed preparations (including human food) or in additives for such preparations.

In a particular embodiment, the fusion-enzyme of the invention can be used for improving the nutritional value of an animal feed. Non-limiting examples of improving the nutritional value of animal feed (including human food), are: Improving feed digestibility; promoting growth of the animal; improving feed utilization; improving bio-availability of proteins; increasing the level of digestible phosphate; improving the release and/or degradation of phytate; improving bio-availability of trace minerals; improving bio-availability of macro minerals; eliminating or reducing the need for adding supplemental phosphate, trace minerals, and/or macro minerals; and/or improving egg shell quality. The nutritional value of the feed is therefore increased, and the growth rate and/or weight gain and/or feed conversion (i.e. the weight of ingested feed relative to weight gain) of the animal may be improved.

Furthermore, the fusion-enzyme of the invention can be used for reducing phytate level of manure.

Animals, Animal Feed, and Animal Feed Additives

The term animal includes all animals, including human beings. Examples of animals are non-ruminants, and ruminants. Ruminant animals include, for example, animals such as sheep, goat, and cattle, e.g. cow such as beef cattle and dairy cows. In a particular embodiment, the animal is a non-ruminant animal. Non-ruminant animals include monogastric animals, e.g. pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

The term feed or feed composition means any compound, preparation, mixture, or composition suitable for, or intended for intake by an animal.

In the use according to the invention the fusion-enzyme can be fed to the animal before, after, or simultaneously with the diet. The latter is preferred.

In a particular embodiment, the fusion-enzyme, in the form in which it is added to the feed, or when being included in a feed additive, is substantially pure. In a particular embodiment it is well-defined. The term "well-defined" means that the enzyme preparation is at least 50% pure as determined by Size-exclusion chromatography (see Example 12 of WO 01/58275). In other particular embodiments the enzyme, for example the phytase preparation is at least 60, 70, 80, 85, 88, 90, 92, 94, or at least 95% pure as determined by this method.

The enzyme preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original polypeptide preparation, whether used according to (a) or (b) above.

In a further aspect the present invention relates to compositions for use in animal feed, such as animal feed additives, e.g. premixes.

Usually fat- and water-soluble vitamins, as well as trace minerals form part of a so-called premix intended for addition to the feed, whereas macro minerals are usually separately added to the feed. Either of these composition types, when enriched with an enzyme of the invention, is an animal feed additive of the invention.

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

Further, optional, feed-additive ingredients are colouring agents, e.g. carotenoids such as beta-carotene, astaxanthin, and lutein; aroma compounds; stabilisers; antimicrobial peptides; polyunsaturated fatty acids; reactive oxygen generating species; and/or at least one other polypeptide selected from amongst phytase (EC 3.1.3.8 or 3.1.3.26); phosphatase (EC 3.1.3.1; EC 3.1.3.2; EC 3.1.3.39); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and polypeptides such as an oxidase, an oxygenase or a syntetase.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one fusion-enzyme as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & Iooijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can e.g. be manufactured as mash feed (non pelleted) or pelleted feed or extruded feed. Typically, the milled feed-stuffs are mixed and sufficient amounts of essential vitamins and minerals are added according to the specifications for the species in question. Fusion enzymes according to the invention can be added as solid or liquid polypeptide formulations. For example, a solid polypeptide formulation is typically added before or during the mixing step; and a liquid polypeptide preparation is typically added after the pelleting step.

The final fusion-enzyme concentration in the diet is within the range of 0.01-200 mg polypeptide protein per kg diet, for example in the range of 5-30 mg polypeptide protein per kg animal diet.

The fusion-enzyme, in particular the fusion-phytase, of the invention should of course be applied in an effective amount, i.e. in an amount adequate for improving solubilisation and/or improving nutritional value of feed. It is at present contemplated that the polypeptide is administered in one or more of the following amounts (dosage ranges): 0.01-200; 0.01-100; 0.5-100; 1-50; 5-100; 10-100; 0.05-50; or 0.10-10—all these ranges being in mg enzyme or phytase polypeptide protein per kg feed (ppm).

For determining mg enzyme or phytase polypeptide protein per kg feed, the enzyme or phytase is purified from the feed composition, and the specific activity of the purified enzyme is determined using a relevant assay.

EXAMPLES

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

General Methodology

In the first paragraphs the general methodology is summarized:

Strains and Plasmids. *Bacillus subtilis* strains of the present invention are derived from strain 1A747 (Bacillus Genetic Stock Center, The Ohio State University, Columbus, Ohio 43210 USA), which is a prototrophic derivative of *B. subtilis* 168 (trpC2) (GenBank AL009126).

Media. Standard minimal medium (MM) for *B. subtilis* contains 1× Spizizen salts, 0.04% sodium glutamate, and 0.5% glucose. Standard solid complete medium is Tryptone Blood Agar Broth (TBAB, Difco). Standard liquid complete medium is Veal Infusion-Yeast Extract broth (VY). The compositions of these media are described below:

TBAB medium: 33 g Difco Tryptone Blood Agar Base (Catalog #0232), 1 L water. Autoclave.

VY medium: 25 g Difco Veal Infusion Broth (Catalog #0344), 5 g Difco Yeast Extract (Catalog #0127), 1 L water. Autoclave.

Minimal Medium (MM): 100 ml 10× Spizizen salts; 10 ml 50% glucose; 1 ml 40% sodium glutamate, qsp 1 L water.

10× Spizizen salts: 140 g $K_2HPO_4$; 20 g $(NH_4)_2SO_4$; 60 g $KH_2PO_4$; 10 g $Na_3$ citrate.$2H_2O$; 2 g $MgSO_4.7H_2O$; qsp 1 L with water.

10× VFB minimal medium (10×VFB MM): 2.5 g Na-glutamate; 15.7 g $KH_2PO_4$; 15.7 g $K_2HPO_4$; 27.4 g $Na_2HPO_4.12H_2O$; 40 g $NH_4Cl$; 1 g citric acid; 68 g $(NH_4)_2SO_4$; qsp 1 L water.

Trace elements solution: 1.4 g $MnSO_4.H_2O$; 0.4 g $CoCl_2.6H_2O$; 0.15 g $(NH_4)_6Mo_7O_{24}.4H_2O$; 0.1 g $AlCl_3.6H_2O$; 0.075 g $CuCl_2.2H_2O$; qsp 200 ml water.

Fe solution: 0.21 g $FeSO_4.7H_2O$; qsp 10 ml water.

$CaCl_2$ solution: 15.6 g $CaCl_2.2H_2O$; qsp 500 ml water.

Mg/Zn solution: 100 g $MgSO_4.7H_2O$; 0.4 g $ZnSO_4.7H_2O$; qsp 200 ml water.

VFB MM medium: 100 ml 10×VFB MM; 10 ml 50% glucose; 2 ml Trace elements solution; 2 ml Fe solution; 2 ml $CaCl_2$ solution; 2 ml Mg/Zn solution; 882 ml sterile distilled water.

MSgg medium to promote biofilm development: 2.5 mM $KH_2PO_4$, 2.5 mM $K_2HPO_4$, 100 mM MOPS, 2 mM $MgCl_2$, 700 μM $CaCl_2$, 50 μM $MnCl_2$, 1 μM $ZnCl_2$, 50 μM $FeCl_3$, 2 μM Thiamine, 0.5% glycerol, 0.5% glutamic acid, 50 μg/ml tryptophan, 50 μg/ml phenylalanine.

Molecular and Genetic Techniques. Standard genetic and molecular biology techniques are generally know in the art and have been previously described. DNA transformation, PBS1 generalized transduction, and other standard *B. subtilis* genetic techniques are also generally know in the art and have been described previously (Harwood and Cutting, 1992).

Protein Purification. Following incubation in VY medium at 37° C. for 24 h, cultures were centrifuged at 6000 rpm for 10 min. In order to concentrate the proteins, ammonium sulfate 80% was added to the supernatant containing the His-tagged protein of interest, through slow addition of at 4° C. After centrifugation at 10,000 rpm for 15 min, pellet proteins were recovered in 5 mL of 20 mM Tris-HCl, 20 mM imidazole, 500 mM NaCl, pH7.4 buffer, before two consecutive dialysis at 4° C. in 1 L of the same buffer. After filtration, concentrated proteins were applied to a histidine affinity chromatography column (HisTrap Fast Flow, GE Healthcare). His-tagged protein of interest was purified according to the manufacturer recommendations and as known by people skilled in the art. Fractions containing the protein of interest, identified through SDS-PAGE, were dialyzed to remove trace of imidazole.

Phytase Activity Assay. *Citrobacter braakii* phytase activity was assessed at 50° C. and pH4 as described by Han Woo et al. (2003). First, 75 μL of sample were incubated at 50° C. with 300 μL of reaction buffer 100 mM $C_4H_6O_4$, 2 mM $C_6H_{18}O_{24}P_6$, 1 mM $CaCl_2$, pH4. Enzymatic reaction was stopped after 30 min by adding 375 μL 15% trichloroacetic acid (v/w). Then the ortho-phosphates, which were released, were measured by incubating 50 μL of the stopped preliminary reaction during 20 min at 50° C. with 450 μL distilled water and 500 μL of a solution 600 mM $H_2SO_4$, 100 mM $C_6H_7NaO_6$, 4 mM$(NH_4)_6Mo_7O_{24}$. Optical density was then measured at 820 nm. The enzymatic activity was then measured according the following formula:

$$\text{Activity}(U/L) = [(OD_{sample} - OD_{blank}) \times \text{dilution factor}] / (\text{coefficient}_{cal} \times 30 \text{ min})$$

Dot Blot Binding Assay. Binding assays to collagen type I and type IV were performed according to the ELISA procedure using primary antibodies anti-HisTag (Santa Cruz Biotechnologies) and secondary anti-rabbit antibodies coupled to peroxidase (Sigma). Revelation was made with ECL Plus kit (GE Healthcare) following recommendations from manufacturer. Proteins were preliminary spotted to a blot according to the dot blot procedure well known of people skilled in the art.

Biofilm Binding Assay. After being purified as described in the "Protein purification" section, the fusion of the biofilm-binding domain TasA of *Bacillus subtilis* to the amino-terminus of the *Citrobacter braakii* phytase was mixed to a preculture of *Bacillus subtilis* BSP1 biofilm former prepared in VY medium overnight. A control was prepared by following the same procedure, but omitting to mix the TasA_BSP1-Phy fusion protein to the preculture of *Bacillus subtilis* BSP1.100 µl of the respective mixtures are poored onto the surface of MSgg medium, supplemented with 0.5% agar. The standing cultures were incubated at 22° C. for 5 days to to induce biofilm formation. The biofilm were then collected with a sterile loop and washed 3 times with a solution made of 20 mM Tris-HCl, 300 mM NaCl and 1 mM CaCl$_2$, in order to eliminate the TasA_BSP1-Phy protein fusion that has not been incorporated into *Bacillus subtilis* BSP1 biofilm. Biofilms were then suspended in reaction buffer for the assay of phytase activity, as described in the "Phytase activity assay" section.

Example 1

Design of Translational Fusion Cna BSP1-Phy

This example describes the synthetic gene designed to over-express the fusion of a Cna-type collagen-binding domain identified in the undomesticated beneficial strain *B. subtilis* BSP1, to the amino-terminus of the *Citrobacter braakii* phytase.

From 5' to 3', the construction contains respectively (Table 1):
- the promoter region from *B. subtilis* amyQ
- the signal peptide from the *B. subtilis* ytwD gene (encoding the 32 first AA)
- *B. subtilis* BSP1 gene sequence encoding a 1076 AA Cna-type collagen-binding protein potentially containing three binding motifs and deleted for its 36 first AA (signal peptide)
- a ten Alanine spacer (including a PvuII restricton site)
- the codon-pair optimized *Citrobacter brakii* phytase gene appA deleted for its first 22 AA (signal peptide)
- a 56 bp sequence containing respectively a thrombine cleavage site, a hexahistidine tag, two successive stop codons and a NheI cleavage site.

TABLE 1

Sequence of the Cna_BSP1-phy translational fusion. BamHI, SalI, PvuII and NheI cloning sites are in bold underlined (SEQ ID NO: 1). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is in italicized lowercase.

cggccgcccagactgtccgctgtgtaaaaaataggaataaagggggggttg ttattattttactgatatgtaaaatataatttgtataagaaaatgagagg gagaggaaattaattaaaaaaggagcgatttacatatgagttatgcagtt tgtagaatgcaaaaagtgaaatcagggGGATCCagaaaggaggtgatcca atgaacacactggcaaactggaagaagttttttgcttgtggcggttatcat TABLE 1-continued Sequence of the Cna_BSP1-phy translational fusion. BamHI, SalI, PvuII and NheI cloning sites are in bold underlined (SEQ ID NO: 1). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is in italicized lowercase.

ttgttttttggttccaattatgacaaaagcggagattgcggaagctgctG

TCGACGTAACGTCCAGTGACAGCCAATTTTTCGATTTGGTAACAGTTAAG

GACGCCAAAGGCCAGATAGTTGACGGATCAAAAGGAAACGAACCGGCACT

AACACCGGGGGACGAAGTGACACTGACATATGAATGGTCATTGAAAAAAG

ACAAAAAAGCAGATAGCGAACAGGATATCAATGTGGAGTTACCTAAAAGC

TTTACATTTGATAAAGGTGCTGAAGGTGAGATCAAATCTGCTGATCAGGT

CATCGGCAGCTATCAAGTGCCGGCGGGCAGCAGCACCATGACAGTAAAAT

TAACAACTGCATCCGCGGATTCTCTTGATGCCAAGGGGACCATTACACTG

CCAGCTAAGTTTACTGCAGATGTAAAAGAAGATGAACATACAGCAGCAGC

CCTTTTTCAGCTAGGCGGAGGCAAAACCCAGCAGGTGATCATTCCTGTTA

AGAAAGAGGAGACACCAGATGCCGAGGCGGAAGAGCCAAAAAACGACTCT

TCTGATACTGCGGGTGATCAGGAAGGGAAAGATGACAAACCTGCACCTTC

AGTCAGCAAGGATCAAAAAGAGGAAGAACAGCAGCCGTCAGATGACTCTA

AGAGCGGCGAAGCCTCTAAGAGTGATGATTCAAAAAAAGTGTCATCCTCA

AGTCAATCAGCTTTCAAAAGCTTGCAAACTGAAGAAAAACAAATCACGCA

ACATATTTTAACTGGCGTGACGTTGACGGACGAAAACGGAAAGCCATATG

ACAAGGGCAATCGCGCCAATACGAATTCTCCGGTGAAAATTTCAATTGAT

TGGGCTATTCCTGACGATTTAGGAAAAACGATCAATGCCGGCGATAAATA

TGAATTTGATTTGCCTAAAGAATTTATTATGCATAATGACATTGTGAACC

GCCGTTAGGCGCCGGAGACACCACCTACGGGACATTTTCTATTGATACGA

CGGACATGTGGTGATGACATTTAACGGCGAGGTAAAAGAAAGTTCTAATG

CAAAGGCACATTGGTTATCAATACGCAGTTCAACGAGAAAAAAATAACGG

TTCGACAACACAAAAGATTCCATTTCCTGTGAATGCCGATACTCCTGAAA

AACAGTTTATTTTAAACCCAATGTGAGTAAAACCATTGATAAATCAGGTG

GCTGGATAAAGGCATCAACCCTGGTAAAGTAACATGGACGGTCGATGTCA

TAAGAAGTTGGATCAAGTCAAAAATGCCAAACTCACGGAAAGCTTTCCAG

TGGCGTAATCTACCGTTCAGTTAAAGTGTATGAACTCAATGTGAACATTG

TGGTTCTGTCAGCAGAGGAAATGAAGTTTCTTCAGGCTACAGTGTTGATT

AAAAGGAAATGTCACATTTGACGGACAATTGATTCAGCCTACCGCCTTG

ATACGAAACCGACATTGACAATGGTGCGAAGCCGAGTGAAGGCGGAAATA

AACGCTGACAAATAAGGCGGCATTCAGCGGAGACAACCTGGAACCCATTT

TGCAGAAGCCACTGTTGCAGCCAAGTATGGAAAAATGATCGCGAAATCAT

GACCGGCTATGATGGAGAATCTCAAACATTCAGTTGGGCTCTTGCATACA

CTACGGTGAGAAACAGATCGACCAATCCAAGGCCAGCATTAAAGATTCTT

TGGAACTGGTGATTTGCATCTTGTGAAAGATTCTTTGAAGGTTATTCCTA

TACCTTTGGTCAGAATGGCAGCGAGCAAGCGGGCAGGCCTTTAAAGGAAG

TABLE 1-continued

Sequence of the Cna_BSP1-phy translational fusion. BamHI, SalI, PvuII and NheI cloning sites are in bold underlined (SEQ ID NO: 1). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is in italicized lowercase.

CGAGGACTACACGCTGATCGATAATGGAAGCGGATTTGAAGTCAAATTTA

TAAAAACGTAACGAGCGCTTACAAAATCACATATCAAACAAAGGTCAACA

CGGAGTGATCATTGATAAATCTACAACATACACCAATAGCGTTGTGACCG

AACAGGGGATTCAAAAGAAGCTTCTGGAATAGCCATTCAGCAAAATCTCA

CAAAGGATATTCAAACGTTGATTATGAGAAGAAGACGGCTGATTGGACGA

TACAGTTAATAAAAATAAATACTTGATGAACAATTGGACTTTGGATGATC

ATTTGAAAGCGGCGGAATGGTTCTGCTTGATGAATCGTTCAAGCTTCAAG

ACACAACGAACAACAAAACATTACAGAAAGACAAAGACTACACGTTAACA

AAAAAACCTGATCATAAAGGCTTTACTTTGGCATTGATCGGGGATTATGC

AAAAACAGACAGTCAATTTAAGATCACTTATACGACAACGTTCAATGCCG

ATTATTCTAACGAAAGCGTTAAGAATACAGCTCAGTCTACATGGACTGAT

CAAAACGGCAATGAGCGCACGAATAAGGTATCAAGCGGTTTTACGCCGAA

TAATCAGACGACAAACAATGGTTTCAAGAACGGTTCATACAACGCGGTTT

CAAAGGAAATCACGTGGAAAATCGGCGTCAATTATAATGGCGAGCCGACG

AAAAACCCTTATATCAAAGATGCCATAACAGATCCTCAGCAATTTGTGCC

GGGTTCCGTTGTGGTTAAGAGCTATACGATCAATAAAAACGGCTCCATCA

CAGAAGGAGACGCGCTGGATCTGCAAGTTTATGATGTCGAAGAGCCTTCT

GCAAAAAATGAACACACTCTGACGGTACACCTTAAAACAGGCGATTCTGT

ACCATATCTGATTGAGTTTAAGACATCACTCAAAGGACAGGTCATTGATC

AGAATCAGTACACAAACAAGGCAACCTACTATAATGACGGTTATGCAGAC

CGCACACTGACGGGCTCTGTTTCAGTTACGAACGGAGGAAGCCTGGTTTT

CAAAGGCGGCAAACAAAATGGAAGCTACATCGATTGGAACATCAATGTCA

ACTCCAGCCAATCAACGCTGGATGACGTAAAAGTTACTGACACGCCGGAT

GAAAATCAAATACTAGATGCAGATTCTTTTAAAGTATATCAAGCAAAATA

TGATGAAAACGGAGTGGTCAAAGACAGCAGCGGAAATCTGACCGCGGGAG

ATGTCGAGCTTCAAAAAGACAAAGACTACACGTTAGACATCAAAACGGAC

AATACAACAGGTGAACAATCGTTTGTCCTGAAATTCATAGGCAGCTATAA

GCAAATTGATCGCGCCTATGTGATCAAATACCGGTCTCTGATTAACATAG

CCGGCACGAGCGGCCATGTTAAAAATAAGGTGTCCATTTCAGGAACAAAT

GTGAAGGAGGGCAGCAGCTGCTGCTGCGGCTGCGGCAGCAGAAGAACAAAA

*CGGCATGAAGCTTGAACGCGTTGTCATTGTCAGCAGACACGGCGTTCGTG*

*CGCCGACAAAATTCACACCGATTATGAAGGATGTGACACCTGACCAATGG*

*CCGCAATGGGATGTGCCGCTCGGCTGGCTGACGCCAAGAGGCGGAGAGCT*

*TGTTTCTGAGCTCGGACAATATCAGCGCTTGTGGTTTACAAGCAAAGGTC*

*TCCTGAATAACCAAACGTGCCCATCTCCAGGACAAGTAGCTGTTATCGCT*

TABLE 1-continued

Sequence of the Cna_BSP1-phy translational fusion. BamHI, SalI, PvuII and NheI cloning sites are in bold underlined (SEQ ID NO: 1). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is in italicized lowercase.

*GACACTGATCAGCGGACAAGAAAAACAGGCGAAGCATTTTTGGCAGGGCT*

*TGCGCCGAAATGCCAAATTCAAGTACACTATCAAAAAGACGAAGAAAAAA*

*ACGACCCGCTGTTCAACCCGGTTAAAATGGGAAAATGCTCGTTTAACACT*

*CTAAAGGTGAAGAATGCGATTTTAGAGCGTGCCGGCGGAAACATTGAGCT*

*TTACACACAGCGCTATCAATCATCTTTCCGTACGCTTGAAAATGTGCTGA*

*ACTTCTCTCAATCTGAAACATGCAAAACAACAGAAAAATCAACAAAATGC*

*ACGCTTCCTGAAGCGCTGCCATCTGAGTTTAAAGTAACGCCTGACAATGT*

*ATCCCTTCCTGGTGCATGGAGCCTTTCCTCAACGCTGACTGAGATTTTCC*

*TATTGCAGGAAGCTCAAGGCATGCCGCAAGTCGCCTGGGGCCGGATTACC*

*GGCGAAAAAGAGTGGAGGGATTTGCTGTCACTTCACAACGCTCAATTTGA*

*CCTTCTTCAGCGTACACCAGAGGTTGCCCGCTCCCGTGCAACCCCGCTTC*

*TTGATATGATTGACACAGCTTTGCTGACAAATGGCACAACTGAAAACCGT*

*TACGGCATCAAACTTCCGGTTTCTCTATTGTTTATTGCAGGGCATGACAC*

*AAACCTTGCCAACCTTTCCGGCGCGCTTGATTTAAAATGGTCGCTGCCAG*

*GACAGCCGGACAATACGCCGCCCGGCGGAGAACTCGTATTTGAAAAATGG*

*AAACGCACTTCTGACAACACTGACTGGGTACAGGTTTCTTTCGTTTATCA*

*AACGCTTCGTGACATGCGTGACATACAGCCGCTCAGCCTTGAAAAGCCTG*

*CCGGAAAAGTAGACTTAAAATTAATCGCATGTGAAGAGAAAAATTCTCAA*

*GGTATGTGCTCGCTGAAATCATTCTCTCGCTTGATTAAAGAAATCCGCGT*

*GCCTGAATGTGCTGTCACAGAGCTGGTGCCGCGCGGCAGCAGCAGCGGC*c accaccaccaccaccacTAATAAGCTAGC

Example 2

Design of Translational Fusion Cna-Phy

This example describes the synthetic gene designed to over-express the fusion of the collagen-binding domain Cna of *Staphyloccus aureus* to the amino-terminus of the *Citrobacter braakii* phytase.

From 5' to 3', the construction contains respectively (Table 2):
- the promoter region from *B. subtilis* amyQ
- the signal peptide from the *B. subtilis* ytwD gene (encoding the 32 first AA)
- *Staphylococcus aureus* cna sequence encoding a 313 AA collagen-binding protein deleted for its 30 first AA (signal peptide)
- a ten Alanine spacer (including a PvuII restriction site)
- the codon-pair optimized *Citrobacter brakii* phytase gene appA deleted for its first 22 AA (signal peptide)
- a 56 bp sequence containing respectively a thrombin cleavage site, a hexahistidine tag, two successive stop codons and a NheI cleavage site.

TABLE 2

Sequence of the Cna-phy translational fusion.
BamHI, SalI, PvuII and NheI cloning sites are in
bold underlined (SEQ ID NO: 2). Alanine spacer
region is underlined uppercase. Codon-pair
optimized phytase sequence is italicized uppercase.
His-tag is in bold lowercase. Stop codons are in
bold uppercase. Peptide signal is in underlined
lowercase. Promoter is in italicized lowercase.

cggccgcccagactgtccgctgtgtaaaaaataggaataaagggggg*ttg*

*ttattattttactgatatgtaaaatataatttgtataagaaaatgagagg*

*gagaggaaattaattaaaaaaggagcgatttacatatgagttatgcagtt*

*tgtagaatgcaaaaagtgaaatcaggg*GGATCCagaaaggaggtgatcca atgaacacactggcaaactggaagaagttttttgcttgtggcggttatcat ttgttttttggttccaattatgacaaaagcggagattgcggaagctgctG

TCGACCGAGATATTTCATCAACGAATGTTACAGATTTAACTGTATCACCG

TCTAAGATAGAAGATGGTGGTAAAACGACAGTAAAAATGACGTTCGACGA

TAAAAATGGAAAAATACAAAATGGTGACATGATTAAAGTGGCATGGCCGA

CAAGCGGTACAGTAAAGATAGAGGGTTATAGTAAAACAGTACCATTAACT

GTTAAAGGTGAACAGGTGGGTCAAGCAGTTATTACACCAGACGGTGCAAC

AATTACATTCAATGATAAAGTAGAAAAATTAAGTGATGTTTCGGGATTTG

CAGAATTTGAAGTACAAGGAAGAAATTTAACGCAAACAAATACTTCAGAT

GACAAAGTAGCTACGATAACATCTGGGAATAAATCAACGAATGTTACGGT

TCATAAAAGTGAAGCGGGAACAAGTAGTGTTTTCTATTATAAAACGGGAG

ATATGCTACCAGAAGATACGACACATGTACGATGGTTTTTAAATATTAAC

AATGAAAAAGTTATGTATCGAAAGATATTACTATAAAGGATCAGATTCA

AGGTGGACAGCAGTTAGATTTAAGCACATTAAACATTAATGTGACAGGTA

CACATAGCAATTATTATAGTGGACAAAGTGCAATTACTGATTTTGAAAAA

GCCTTTCCAGGTTCTAAAATAACTGTTGATAATACGAAGAACACAATTGA

TGTAACAATTCCACAAGGCTATGGGTCATATAATAGTTTTTCAATTAACT

ACAAAACCAAAATTACGAATGAACAGCAAAAAGAGTTTGTTAATAATTCA

CAAGCTTGGTATCAAGAGCATGGTAAGGAAGAAGTGAACGGGAAATCATT

TAATCATACTGTGCACAATATTAATGCTAATGCCGGTATTGAAGGTACTG

TAAAAGGTGAATTAAAAGTTTTAAAACAGGATAAAGATACCAAGGCTGCA

GCAGCTGCTGCTGCGGCTGCGGCAGCA*GAAGAACAAAACGGCATGAAGCT*

*TGAACGCGTTGTCATTGTCAGCAGACACGGCGTTCGTGCGCCGACAAAAT*

*TCACACCGATTATGAAGGATGTGACACCTGACCAATGGCCGCAATGGGAT*

*GTGCCGCTCGGCTGGCTGACGCCAAGAGGCGGAGAGCTTGTTTCTGAGCT*

*CGGACAATATCAGCGCTTGTGGTTTACAAGCAAAGGTCTCCTGAATAACC*

*AAACGTGCCCATCTCCAGGACAAGTAGCTGTTATCGCTGACACTGATCAG*

*CGGACAAGAAAAACAGGCGAAGCATTTTTGGCAGGGCTTGCGCCGAAATG*

*CCAAATTCAAGTACACTATCAAAAAGACGAAGAAAAAAACGACCCGCTGT*

*TCAACCCGGTTAAAATGGGAAAATGCTCGTTTAACACTCTAAAGGTGAAG*

*AATGCGATTTTAGAGCGTGCCGGCGGAAACATTGAGCTTTACACACAGCG*

*CTATCAATCATCTTTCCGTACGCTTGAAAATGTGCTGAACTTCTCTCAAT*

TABLE 2-continued

Sequence of the Cna-phy translational fusion.
BamHI, SalI, PvuII and NheI cloning sites are in
bold underlined (SEQ ID NO: 2). Alanine spacer
region is underlined uppercase. Codon-pair
optimized phytase sequence is italicized uppercase.
His-tag is in bold lowercase. Stop codons are in
bold uppercase. Peptide signal is in underlined
lowercase. Promoter is in italicized lowercase.

*CTGAAACATGCAAAACAACAGAAAAATCAACAAAATGCACGCTTCCTGAA*

*GCGCTGCCATCTGAGTTTAAAGTAACGCCTGACAATGTATCCCTTCCTGG*

*TGCATGGAGCCTTTCCTCAACGCTGACTGAGATTTTCCTATTGCAGGAAG*

*CTCAAGGCATGCCGCAAGTCGCCTGGGGCCGGATTACCGGCGAAAAAGAG*

*TGGAGGGATTTGCTGTCACTTCACAACGCTCAATTTGACCTTCTTCAGCG*

*TACACCAGAGGTTGCCCGCTCCCGTGCAACCCCGCTTCTTGATATGATTG*

*ACACAGCTTTGCTGACAAATGGCACAACTGAAAACCGTTACGGCATCAAA*

*CTTCCGGTTTCTCTATTGTTTATTGCAGGGCATGACACAAACCTTGCCAA*

*CCTTTCCGGCGCGCTTGATTTAAAATGGTCGCTGCCAGGACAGCCGGACA*

*ATACGCCGCCCGGCGGAGAACTCGTATTTGAAAAATGGAAACGCACTTCT*

*GACAACACTGACTGGGTACAGGTTTCTTTCGTTTATCAAACGCTTCGTGA*

*CATGCGTGACATACAGCCGCTCAGCCTTGAAAAGCCTGCCGGAAAAGTAG*

*ACTTAAAATTAATCGCATGTGAAGAGAAAAATTCTCAAGGTATGTGCTCG*

*CTGAAATCATTCTCTCGCTTGATTAAAGAAATCCGCGTGCCTGAATGTGC*

*TGTCACAGAGCTGGTGCCGCGCGGCAGCAGCAGCGGC*caccaccaccaca ccacTAATAAGCTAGC

Example 3

Construction of *B. subtilis* Strain Expressing the Fusion Cna BSP1-Phy

This example describes the construction of *B. subtilis* strain BSPB29 designed to overexpress the Cna_BSP1-phy fusion.

The cna_BSP1-phy synthetic gene was inserted into a multicopy plasmid then transformed into a protease-deficient *B. subtilis* strain as known by people skilled in the art.

Example 4

Construction of *B. subtilis* Strain Expressing the Fusion Cna-Phy

This example describes the construction of *B. subtilis* strain BSPB32 designed to over-express the Cna-phy.

The Cna-phy synthetic gene was inserted on a multicopy plasmid then transformed into a protease-deficient *B. subtilis* strain as known by people skilled in the art.

Example 5

Design of Translational Fusion Cna Dd-Amy

This example describes the synthetic gene designed to over-express the fusion of the collagen-binding domain Cna of *Denitrobacterium detoxificans* (courtesy from Dr. Stanton, National Animal Disease Ctr, USDA-Agricultural Research Service, Ames, Iowa, USA) to the amino-terminus of an α-amylase.

From 5' to 3', the construction contains respectively (Table 3):
- the promoter region from *B. subtilis* amyQ
- the signal peptide from the *B. subtilis* ytwD gene (encoding the 32 first AA)
- *Denitrobacterium detoxificans* Dd01g014920 sequence encoding a 771 AA collagen-binding protein
- a ten Alanine spacer (including a PvuII restriction site)
- the *Bacillus licheniformis* α-amylase gene amyL deleted for its first 38 AA (signal peptide)
- a 56 bp sequence containing respectively a thrombin cleavage site, a hexahistidine tag, two successive stop codons and a NheI cleavage site.

TABLE 3

Sequence of the Cna_Dd-amy translational fusion. BamHI, SalI, PvuII and NheI cloning sites are in bold underlined (SEQ ID NO: 3). Alanine spacer region is underlined uppercase. *B. licheniformis* α-amylase sequence is lowercase. His-tag is in bold lowercase. Stop codons are in bold uppercase. Peptide signal is in underlined lowercase. Promoter is in italicized bold lowercase.

cggccgcccagactgtccgctgtgtaaaaaataggaataaaggggggttg ttattattttactgatatgtaaaatataatttgtataagaaaatgagagg gagaggaaattaattaaaaaaggagcgatttacatatgagttatgcagtt tgtagaatgcaaaaagtgaaatcagggGGATCCagaaaggaggtgatcca atgaacacactggcaaactggaagaagttttgcttgtggcggttatcat ttgttttttggttccaattatgacaaaagcggagattgcggaagctgctG

TCGACGTGCGCATCGCACCACGCGGCAGGATAGAGCTGCAAAAGGAATCG

TCGAACGCATCAATTACCGGCGGGAATGCATGCTATTCCCTACAAGGAGC

CGAATTCGAAGTGCGGGACGCCTCGGGCAATCATGCCACGACGCTCGTTA

CCGACGAACGGGATACGCACGTTCGGGCGATCTGCTCTGCGGCACGTAC

ACCGTACGGGAAACGAAGGCGCCCAGGGGATACGCACTGAGCGGAAGGGA

GTTTCGCGTAACCGTTACGCCCAACACCACCACACGCGTAGCGGGAACAG

GAGGCGTGATTACCGACGAACCATTGGGAAACCCCATCGACCTGCTTCTG

CGCAAAACGGACCCCCAAACGGGCAGCCATCCGCAAGGCGCAGGCTCCTT

GGCGGGGGCACGTTTCACCGTGCGCTATTACGATGGCTACTACGACCAGG

GAAATCTTCCATCCACCGCCATCCGATCCTGGACGTTCGAAACCGACGAA

CGAGGAGAAGTTCATTTCAGCGACTCATACCTGAAGCAAGGCGACGCGCT

TTATCGCAACGCCAAGAAGCAACCCATCGTGCCCCTGGGCACCATAACCA

TCCAAGAGGTGCAGGCTCCTGCGGGGTACGCACTCGACGATGGCGCGGGA

CATGCCACACCACTTCACGTCGTGCGCATCACCAGCGACAACACGAATGC

AACATCGACCGATATCGCATGCTACGCCCCATTCGACCAACCCGACAGCG

TGCAACGGGGCGATTTCAGGCTCGTGAAAAAGGTCGCATCCGAAGCGGGC

ATCGACGAGCTGGCGACAGGAGTTCAATTCCAAATCATCAACGAGAACGG

CCACGACGTTGCCTCACCAGAGCCCGGCAATGCCCTGGTGAAAAAAGGCG

ATGCCGTCTGCACCATCACCGTCGATGCAAACGGCCTGGCATCCACGCGC

TABLE 3-continued

Sequence of the Cna_Dd-amy translational fusion. BamHI, SalI, PvuII and NheI cloning sites are in bold underlined (SEQ ID NO: 3). Alanine spacer region is underlined uppercase. *B. licheniformis* α-amylase sequence is lowercase. His-tag is in bold lowercase. Stop codons are in bold uppercase. Peptide signal is in underlined lowercase. Promoter is in italicized bold lowercase.

AATGAAGCCGCCAACGGCTGGGCCACGCCAGCAAGCTGGGCTGGGGCACT

CGCGTACGGAACGTACCGCATTCACGAAGTCATTCCCAGCGAAGTACAGC

GCGCATTCGGCGAAGCGCACGCAGGGGCAACCATCGCCACCGTGCCCGAC

TGGCGCATCACGATAGGCGCCAACAGGCAATACGACGCGCCCGCACTCGT

CACCGACACCGTGCCCCAATCGCCCTTGAAGGTGGTGAAGATCGACGGCG

AAACAGGCAAGCCCATTCCCCTACCCTGTTCGTTTCAGCTCTACGACCAG

AGTGGATGCCTCGTTACCTACGAAGCGCATTACCCCGAACCAACCACCAT

GGACACGTGGACCACACAAATGACTCTGGAGAGGCAACGCTGCCCATGATGC

TCCACGACGGCACGTATACGCTGAAGGAAATACAGGCGCCCGCAGGCTAC

ATCCTCGACCCCGACCCCGTGCCCTTCACCGTGGACAGCACGTCGCGCAC

CTGGGACAACCCCCTGGTAATCACCATTGCGAACCAACCGGCAAAGGGGA

CGATTGCCCTTTCGAAGAGCGACGACGTAACGGGTACGGGCATCGCCGGG

GCGCAATACAACATATGCGCCGCAAGCGACATAGCAACGCCCGACGGCAC

CATACGCGCTCATGAAGGCGATATAGTGGCCCAGCTTACATGCGGCGAAG

ACGGTACCGCACATTCAGACGAACTCTACCTGGGGTCATATCGGTTCTAC

GAAACCAAAGCCCCGAACGGATACGCACTCGACCCCGAGGAGCACCCCGT

AGAGCTCACGAATGAGGGCCAGCACGAAACCACAACGGTCGCCCCCGCAG

CAACCACCGACGAACCCACCTCATTGCGCATCCTGAAAACCTGCTCGGAA

ACGGACAAGCCACTTGCAGGAGCAACATTCTCGATTGCAAGCGAGGACGC

AACCACGGAGCCAATGCAACTGGAAACAGATGCTAACGGCGTGGCCTACA

TCGAACACCTGGGGCATGGCTCGTATTGCATACGGGAAACGAAAGCCCCA

CCCGGTTGGCTCATAAGCGAGGATGCCGCGCAGGGAACGTGCTTCACCGT

AAACGACCAGGGATTCATTTGCATGGAAGGGGCCAGCGAATTAGCAAGCG

AGGTCACGCTCAACGTGGAAAACGAGCCAAAACCACCCGAAGCGCCCATT

CCAAGGGAACTCCCAAAGCCAGCCCACGCTTCCCCACCTACGCATGACAA

TGCGGCAGGAGCGGTATGCGCCATCGTCGCATGCATGATCATGACGCTTG

CCGTGGCACGTGCCGCCCAACGCGCCGCGCAAGAGACCCCAAGCCGAAG

CAAACGCGCCTACGGAGGAAAGCAGCAGCTGCTGCTGCGGCTGCGGCAGC

Agcggcaaatcttaatgggacgctgatgcagtattttgaatggtacatgc ccaatgacggccaacattggaagcgtttgcaaaacgactcggcatatttg gctgaacacggtattactgccgtctggattccccggcatataagggaac gagccaagcggatgtgggctacggtgcttacgacctttatgatttaggg agtttcatcaaaaagggacggttcggacaaagtacggcacaaaaggagag ctgcaatctgcgatcaaaagtcttcattcccgcgacattaacgtttacgg ggatgtggtcatcaaccacaaaggcggcgctgatgcgaccgaagatgtaa ccgcggttgaagtcgatcccgctgaccgcaaccgcgtaaatttcaggagaa

TABLE 3-continued

Sequence of the Cna_Dd-amy translational fusion.
BamHI, SalI, PvuII and NheI cloning sites are
in bold underlined (SEQ ID NO: 3). Alanine spacer
region is underlined uppercase. *B. licheniformis*
α-amylase sequence is lowercase. His-tag is in
bold lowercase. Stop codons are in bold uppercase.
Peptide signal is in underlined lowercase.
Promoter is in italicized bold lowercase.

cacctaattaaagcctggacacattttcattttccggggcgcggcagcac atacagcgattttaaatggcattggtaccattttgacggaaccgattggg acgagtcccgaaagctgaaccgcatctataagtttcaaggaaaggcttgg gattgggaagtttccaatgaaaacggcaactatgattatttgatgtatgc cgacatcgattatgaccatcctgatgtcgcagcagaaattaagagatggg gcacttggtatgccaatgaactgcaattggacggtttccgtcttgatgct gtcaaacacattaaatttttcttttttgcgggattgggttaatcatgtcag ggaaaaaacggggaaggaaatgtttacggtagctgaatattggcagaatg acttgggcgcgctggaaaactatttgaacaaaacaaattttaatcattca gtgtttgacgtgccgcttcattatcagttccatgctgcatcgacacaggg aggcggctatgatatgaggaaattgctgaacggtacggtcgtttccaagc atccgttgaaatcggttacatttgtcgataaccatgatacacagccgggg caatcgcttgagtcgactgtccaaacatggtttaagccgcttgcttacgc ttttattctcacaagggaatctggatacccctcaggttttctacggggata tgtacgggacgaaaggagactcccagcgcgaaattcctgccttgaaacac aaaattgaaccgatcttaaaagcgagaaaacagtatgcgtacggagcaca gcatgattatttcgaccaccatgacattgtcggctggacaagggaaggcg acagctcggttgcaaattcaggtttggcggcattaataacagacggaccc ggtggggcaaagcgaatgtatgtcggccggcaaaacgccggtgagacatg gcatgacattaccggaaaccgttcggagccggttgtcatcaattcggaag gctggggagagtttcacgtaaacggcgggtcggtttcaatttatgttcaa agatagTGGTGCCGCGCGGCAGCAGCAGCGGCcaccaccaccacaccacT

AATAA<u>GCTAGC</u>

Example 6

Collagen-Affinity Binding of the Cna BSP1-Phy Fusion

This example demonstrates in vitro binding of the purified Cna_BSP1-phy fusion to collagen type I and type IV.

FIG. 1 shows a dot blot with Cna_BSP1-phy fusion. Different decreasing amounts of collagens have been spotted on membrane before being incubated with a constant amount of Cna_BSP1-phy fusion (5 nM). Revelation was made by ELISA using a primary antibody directed against the his-tag of the translational fusion.

Example 7

Collagen-Affinity Binding of the Cna-Phy Fusion

This example demonstrates in vitro binding of the purified Cna-phy fusion to collagen type I and type IV.

Figure 2:
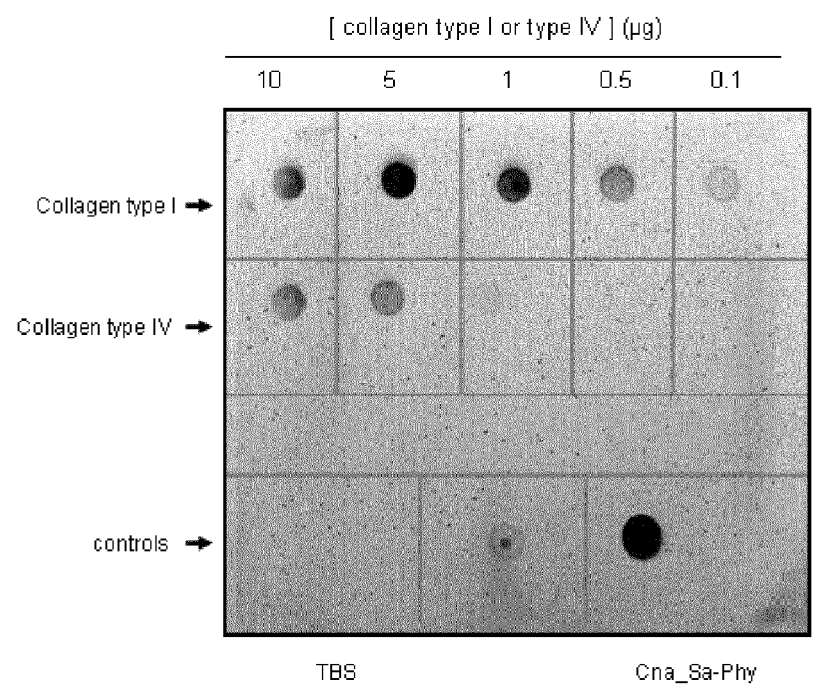

FIG. 2 shows a dot blot with Cna-phy fusion. Different decreasing amounts of collagen have been spotted on membrane before being incubated with a constant amount of Cna-phy fusion (5 nM). Revelation was made by ELISA using a primary antibody directed against the his-tag of the translational fusion.

Example 8

Affinity Spectrum of Cna-BSP1-Phy

This example demonstrates that fusions containing collagen-binding domains are also able to bind in vitro to other extracellular matrix (ECM) proteins, namely laminin, fibronectin and fibrinogen.

Figure 3:
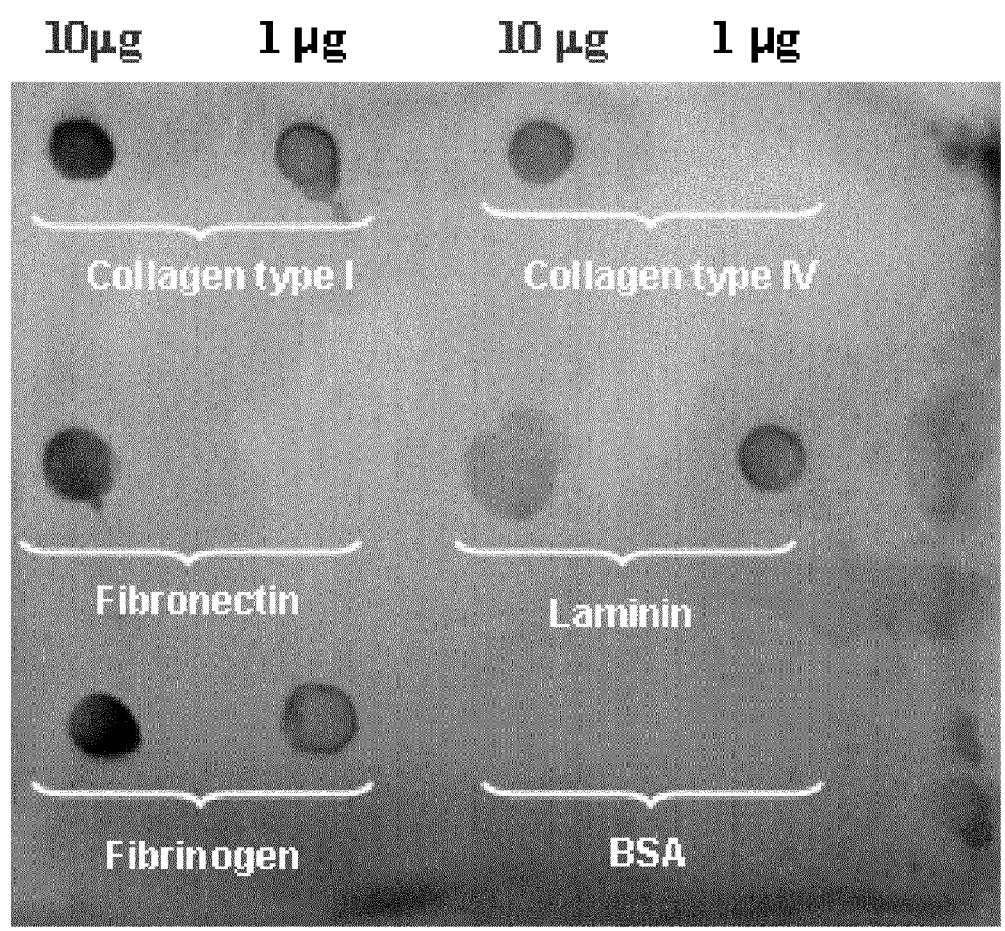

FIG. 3 shows a dot blot with Cna_BSP1-phy fusion. Two different amounts of extracellular matrix (ECM) proteins have been spotted on membrane before being incubated with a constant amount of Cna_BSP1-phy fusion (5 nM). Revelation was made by ELISA using a primary antibody directed against the his-tag of the translational fusion.

Example 9

Phytase Activity of Collagen-Bound Cna-Phy Fusion

This example demonstrates that fusions bound to collagens exhibit significant phytase activity.

Figure 4:
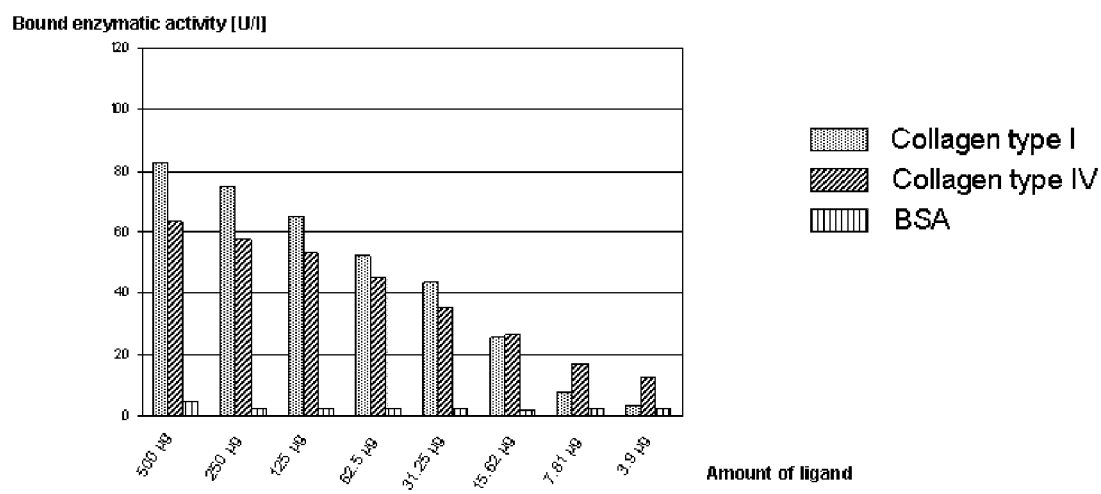

FIG. 4 shows the histograms of phytase enzymatic activity bound to collagen type I and IV. Different amounts of target collagen as mentioned on FIG. 4 have been coated on microtiterplate before being incubated with a constant amount of Cna-phy fusion (50 nM). After washing, phytase activity of the collagen-bound fusion was assessed as described in General methodology. The collagen-bound phytase activity is significantly higher than the one observed after incubation in wells coated with BSA (10 µg)

Example 10

Design of Translational Fusion CBD-Phy

This example describes the synthetic gene designed to over-express the fusion of the collagen-binding domain CBD of *Clostridium histolyticum* collagenase to the amino-terminus of the *Citrobacter braakii* phytase.

From 5' to 3', the construction contains respectively (Table 4):
- the promoter region from *B. subtilis* amyQ
- the signal peptide from the *B. subtilis* ytwD gene (encoding the 32 first AA)
- *Clostridium histolyticum* sequence encoding 215 AA from S2B and S3 domains of colH (Yoshihara et al., 1994)
- a ten Alanine spacer (including a PvuII restriction site)
- the codon-pair optimized *Citrobacter brakii* phytase gene appA deleted for its first 22 AA (signal peptide)
- a 56 bp sequence containing respectively a thrombin cleavage site, a hexahistidine tag, two successive stop codons and a NheI cleavage site.

TABLE 4

Sequence of the CBD-phy translational fusion. BamHI, SalI, PvuII and NheI cloning sites are in bold underlined (SEQ ID NO: 4). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is in italicized lowercase.

cggccgcccagactgtccgctgtgtaaaaaataggaataaagggggg*ttg*

*ttattattttactgatatgtaaaatataatttgtataagaaaatgagagg*

*gagaggaaattaattaaaaaaggagcgatttacatatgagttatgcagtt*

*tgtagaatgcaaaaagtgaaatcaggg*GGATCC*agaaaggaggtgatcca*

<u>atgaacacactggcaaactggaagaagttttttgcttgtggcggttatcat</u>

<u>ttgttttttggttccaattatgacaaaagcggagattgcggaagctgct</u>g tcgacGAAATAAAGGATCTTTCAGAAAATAAACTTCCAGTTATATATG

CATGTACCTAAATCCGGAGCCTTAAATCAAAAGTTGTTTTCTATGGAA

AGGAACATATGACCCAGATGGATCTATCGCAGGATATCAATGGGACTTTG

GTGATGGAAGTGATTTTAGCAGTGAACAAAACCCAAGCCATGTATATACT

AAAAAAGGTGAATATACTGTAACATTAAGAGTAATGGATAGTAGTGGACA

AATGAGTGAAAAAACTATGAAGATTAAGATTACACATCCGGTATATCCAA

TAGGCACTGAAAAAGAACCAAATAACAGTAAAGAAACTGCAAGTGGTCCA

ATAGTACCAGGTATACCTGTTAGTGGAACCATAGAAAATACAAGTGATCA

AGATTATTTCTATTTTGATGTTATAACACCAGGAGAAGTAAAAATAGATA

TAAATAAATTAGGGTACGGAGGAGCTACTTGGGTAGTATATGATGAAAAT

AATAATGCAGTATCTTATGCCACTGATGATGGGCAAAATTTAAGTGGAAA

GTTTAAGGCAGATAAACCAGGTAGATATTACATCCATCTTTACATGTTTA

ATGGTAGTTATATGCCATATAGAATTAATATAGAAGGTTCAGTAGGAAGA

<u>GCAGCAGCTGCTGCTGCGGCTGCGGCAGCA</u>GAAGAACAAAACGGCATGAA

*GCTTGAACGCGTTGTCATTGTCAGCAGACACGGCGTTCGTGCGCCGACAA*

*AATTCACACCGATTATGAAGGATGTGACACCTGACCAATGGCCGCAATGG*

*GATGTGCCGCTCGGCTGGCTGACGCCAAGAGGCGGAGAGCTTGTTTCTGA*

*GCTCGGACAATATCAGCGCTTGTGGTTTACAAGCAAAGGTCTCCTGAATA*

*ACCAAACGTGCCCATCTCCAGGACAAGTAGCTGTTATCGCTGACACTGAT*

*CAGCGGACAAGAAAAACAGGCGAAGCATTTTTGGCAGGGCTTGCGCCGAA*

*ATGCCAAATTCAAGTACACTATCAAAAAGACGAAGAAAAAAACGACCCGC*

*TGTTCAACCCGGTTAAAATGGGAAAATGCTCGTTTAACACTCTAAAGGTG*

*AAGAATGCGATTTTAGAGCGTGCCGGCGGAAACATTGAGCTTTACACACA*

*GCGCTATCAATCATCTTTCCGTACGCTTGAAAATGTGCTGAACTTCTCTC*

*AATCTGAAACATGCAAAACAACAGAAAAATCAACAAAATGCACGCTTCCT*

*GAAGCGCTGCCATCTGAGTTTAAAGTAACGCCTGACAATGTATCCCTTCC*

*TGGTGCATGGAGCCTTTCCTCAACGCTGACTGAGATTTTCCTATTGCAGG*

*AAGCTCAAGGCATGCCGCAAGTCGCCTGGGGCCGGATTACCGGCGAAAAA*

*GAGTGGAGGGATTTGCTGTCACTTCACAACGCTCAATTTGACCTTCTTCA*

*GCGTACACCAGAGGTTGCCCGCTCCCGTGCAACCCCGCTTCTTGATATGA*

TABLE 4-continued

Sequence of the CBD-phy translational fusion. BamHI, SalI, PvuII and NheI cloning sites are in bold underlined (SEQ ID NO: 4). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is in italicized lowercase.

*TTGACACAGCTTTGCTGACAAATGGCACAACTGAAAACCGTTACGGCATC*

*AAACTTCCGGTTTCTCTATTGTTTATTGCAGGGCATGACACAAACCTTGC*

*CAACCTTTCCGGCGCGCTTGATTTAAAATGGTCGCTGCCAGGACAGCCGG*

*ACAATACGCCGCCCGGCGGAGAACTCGTATTTGAAAAATGGAAACGCACT*

*TCTGACAACACTGACTGGGTACAGGTTTCTTTCGTTTATCAAACGCTTCG*

*TGACATGCGTGACATACAGCCGCTCAGCCTTGAAAAGCCTGCCGGAAAAG*

*TAGACTTAAAATTAATCGCATGTGAAGAGAAAAATTCTCAAGGTATGTGC*

*TCGCTGAAATCATTCTCTCGCTTGATTAAAGAAATCCGCGTGCCTGAATG*

*TGCTGTCACAGAGCTGGTGCCGCGCGGCAGCAGCAGCGGC*caccaccacc acaccacTAATAA<u>GCTAGC</u>

Example 11

Design of Translational Fusion MubBP(RI+RII)-phy

This example describes the synthetic gene designed to over-express the fusion of the mucin-binding domain of *Lactobacillus reuteri* 1063 to the amino-terminus of the *Citrobacter braakii* phytase.

From 5' to 3', the construction contains respectively (Table 5):
- the promoter region from *B. subtilis* amyQ
- the signal peptide from the *B. subtilis* ytwD gene (encoding the 32 first AA)
- *Lactobacillus reuteri* 1063 Mub1 (RI+RII repeats) 390 AA between position 549 and position 939 in the sequence Genebank AF120104 (Roos and Jonsson, 2002)
- a ten Alanine spacer (including a PvuII restriction site)
- the codon-pair optimized *Citrobacter brakii* phytase gene appA deleted for its first 22 AA (signal peptide)
- a 56 bp sequence containing respectively a thrombine cleavage site, a hexahistidine tag, two successive stop codons and a NheI cleavage site.

TABLE 5

Sequence of the MubBP(RI + RII)-phy translational fusion. BamHI, SalI, PvuII and NheI cloning sites are in bold underlined (SEQ ID NO: 5). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is in italicized lowercase.

cggccgcccagactgtccgctgtgtaaaaaataggaataaagggggg*ttg*

*ttattattttactgatatgtaaaatataatttgtataagaaaatgagagg*

TABLE 5-continued

Sequence of the MubBP(RI + RII)-phy translational fusion. BamHI, SalI, PvuII and NheI cloning sites are in bold underlined (SEQ ID NO: 5). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is in italicized lowercase.

*gagaggaaattaattaaaaaaggagcgatttacatatgagttatgcagtt*

*tgtagaatgcaaaaagtgaaatcaggg*GGATCC*agaaaggaggtgatcca* atgaacacactggcaaactggaagaagttttttgcttgtggcggttatcat ttgtttttggttccaattatgacaaaagcggagattgcggaagctgctg tcgacGTTGTTTATGTAGCTGACACGCAAGAAGCTGCCATCAGCTTCTAT

GACGAGACAGACCACAAGCCACTGAATGACCAAACGATTCAGCAGACTGG

CAAGACTGGTGAAAAGATCAGCCATACCGAAGCTAATCAAACACTGGCTA

AGCTGGGAAAGCAAGGCTATGTTGTAGACCAGAATACTTTTGCTGATGAT

GCAACGTATGACAACGATACGCAAGCACCACAAGAGTTTACGATCTACCT

CAAGCATGATACGACCCATACTGACGCAACTAGCTCAAAGGCAGATCAAA

AGACCGTCAGCGAAACGATTCACTACGTCTACAAAGATGGGGTCAACGCT

AATAAGCCGGTAGCTGATGACGCTAATACAACGGTTACCTTCAAACGCGG

CTACACGACTGACAAAGTTACGGGAAAGATTGTTTCCTATGATCCTTGGA

CGGTTGATGGCAAGCAAGCCGACAGCAAGACGTTTGATGCCGTCAAGAGT

CCAGTCATTGCTGGTTACACGGCCGATCAAGCAGAAGTTGCCGCTCAAAC

GGTAACGCCAGATTCCCAAAATATTAACAAGACAGTTTACTATACCGCTG

ACACGCAAGAAGCTGCCATCAACTTCTATGACGAGACAGGCCACAAGCTG

TTAGATAACCAAACGATTCATTTGACTGGCAAGACCGGTGAAAAGGTAGA

CCGGACGCAAGCGGACCAGACGTTGGCTGATCTGGTAAAGCAAGGCTATG

TTTTGGATAAAGAAAACACGGCCAAGGCATTCCCAGCTAACGCGGTATAT

GACAACAATGACCAAACGCCACAAGAGTTTACGATCTACCTCAAGCATGG

TACGACCCATACTGACGCAACCAGCTCAAAGGCAGATCAAAAGACCGTCA

GCGAAACGATTCACTACGTCTACAAAGATGGGGTCAACGCTAATAAGCCG

GTAGCTGATGACGCTAATACAACGGTTACCTTCAAACGCGGCTACACGAC

TGACAAAGTTACGGGAAAGATTGTTTCCTATGATCCTTGGACGGTTGATG

GCAAGCAAGCCGACAGCAAGACGTTTGATGCCGTCAAGAGTCCAGTCATT

GCTGGTTACACGGCCGATCAAGCAGAAGTTGCCGCTCAAACGGTAACGCC

AGATTCCCAAAATATTAACAAGACACAGCTGCTGCTGCGGCTGCGGCAGC

AGAAGAACAAAACGGCATGAAGCTTGAACGCGTTGTCATTGTCAGCAGAC

*ACGGCGTTCGTGCGCCGACAAAATTCACACCGATTATGAAGGATGTGACA*

*CCTGACCAATGGCCGCAATGGGATGTGCCGCTCGGCTGGCTGACGCCAAG*

*AGGCGGAGAGCTTGTTTCTGAGCTCGGACAATATCAGCGCTTGTGGTTTA*

*CAAGCAAAGGTCTCCTGAATAACCAAACGTGCCCATCTCCAGGACAAGTA*

*GCTGTTATCGCTGACACTGATCAGCGGACAAGAAAAACAGGCGAAGCATT*

*TTTGGCAGGGCTTGCGCCGAAATGCCAAATTCAAGTACACTATCAAAAAG*

TABLE 5-continued

Sequence of the MubBP(RI + RII)-phy translational fusion. BamHI, SalI, PvuII and NheI cloning sites are in bold underlined (SEQ ID NO: 5). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is in italicized lowercase.

*ACGAAGAAAAAAACGACCCGCTGTTCAACCCGGTTAAAATGGGAAAATGC*

*TCGTTTAACACTCTAAAGGTGAAGAATGCGATTTTAGAGCGTGCCGGCGG*

*AAACATTGAGCTTTACACACAGCGCTATCAATCATCTTTCCGTACGCTTG*

*AAAATGTGCTGAACTTCTCTCAATCTGAAACATGCAAAACAACAGAAAAA*

*TCAACAAAATGCACGCTTCCTGAAGCGCTGCCATCTGAGTTTAAAGTAAC*

*GCCTGACAATGTATCCCTTCCTGGTGCATGGAGCCTTTCCTCAACGCTGA*

*CTGAGATTTTCCTATTGCAGGAAGCTCAAGGCATGCCGCAAGTCGCCTGG*

*GGCCGGATTACCGGCGAAAAAGAGTGGAGGGATTTGCTGTCACTTCACAA*

*CGCTCAATTTGACCTTCTTCAGCGTACACCAGAGGTTGCCCGCTCCCGTG*

*CAACCCCGCTTCTTGATATGATTGACACAGCTTTGCTGACAAATGGCACA*

*ACTGAAAACCGTTACGGCATCAAACTTCCGGTTTCTCTATTGTTTATTGC*

*AGGGCATGACACAAACCTTGCCAACCTTTCCGGCGCGCTTGATTTAAAAT*

*GGTCGCTGCCAGGACAGCCGGACAATACGCCGCCCGGCGGAGAACTCGTA*

*TTTGAAAAATGGAAACGCACTTCTGACAACACTGACTGGGTACAGGTTTC*

*TTTCGTTTATCAAACGCTTCGTGACATGCGTGACATACAGCCGCTCAGCC*

*TTGAAAAGCCTGCCGGAAAAGTAGACTTAAAATTAATCGCATGTGAAGAG*

*AAAAATTCTCAAGGTATGTGCTCGCTGAAATCATTCTCTCGCTTGATTAA*

*AGAAATCCGCGTGCCTGAATGTGCTGTCACAGAGCTGGTGCCGCGCGGCA*

GCAGCAGCGGCcaccaccaccacaccacTAATAA<u>GCTAGC</u>

Example 12

Production of the Fusion MubBP(RI+RII)-phy

This example describes the construction of *B. subtilis* strain BSPB33 designed to over-express the MubBP(RI+RII)-phy and its purification.

The MubBP(RI+RII)-phy synthetic gene was inserted on a multicopy plasmid then transformed into a protease-deficient *B. subtilis* strain as known by people skilled in the art. After purification according to the procedure described into the General Methodology section, a MubBP(RI+RII) fusion was obtained with a specific phytase activity of 3500 U/g.

Example 13

Mucin-Affinity Binding of the MubBP(RI+RII)-Phy Fusion

This example demonstrates in vitro binding of the purified MubBP(RI+RII)-phy fusion to mucin.

Figure 5:
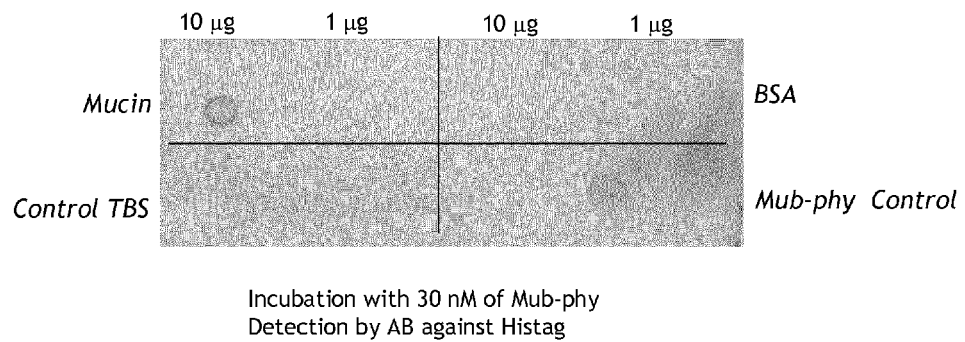

FIG. 5 shows a dot blot with MubBP(RI+RII)-phy fusion. Two different amounts of mucin have been spotted on membrane before being incubated with a constant amount of MubBP(RI+RII)-phy fusion (30 nM). Revelation was made by ELISA using a primary antibody directed against the his-tag of the translational fusion.

Example 14

Design of Translational Fusion MubBP(R5+R6)-Phy

This example describes the synthetic gene designed to over-express the fusion of the mucin-binding domain R5 and R6 of *Lactobacillus reuteri* 1063 to the amino-terminus of the *Citrobacter braakii* phytase.

From 5' to 3', the construction contains respectively (Table 6):

- the promoter region from *B. subtilis* amyQ
- the signal peptide from the *B. subtilis* ytwD gene (encoding the 32 first AA)
- *Lactobacillus reuteri* 1063 R5+R6 repeats 370 AA between position 2105 and position 2475 in the sequence Genebank AF120104 (Roos and Jonsson, 2002)
- a ten Alanine spacer (including a PvuII restriction site)
- the codon-pair optimized *Citrobacter brakii* phytase gene appA deleted for its first 22 AA (signal peptide)
- a 56 bp sequence containing respectively a thrombine cleavage site, a hexahistidine tag, two successive stop codons and a NheI cleavage site.

TABLE 6

Sequence of the MubBP(R5 + R6)-phy translational fusion. BamHI, SalI, PvuII and NheI cloning sites are in bold underlined (SEQ ID NO: 6). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is initalicized lowercase.

cggccgcccagactgtccgctgtgtaaaaaataggaataaaggggggttg ttattattttactgatatgtaaaatataatttgtataagaaaatgagagg gagaggaaattaattaaaaaaggagcgatttacatatgagttatgcagtt tgtagaatgcaaaaagtgaaatcagggGGATCCagaaaggaggtgatcca atgaacacactggcaaactggaagaagttttttgcttgtggcggttatcat ttgttttttggttccaattatgacaaaagcggagattgcggaagctgctg tcgacAGAAAGGAGGTGATCCAATGAACACACTGGCAAACTGGAAGAAGT

TTTTGCTTGTGGCGGTTATCATTTGTTTTTTGGTTCCAATTATGACAAAA

GCGGAGATTGCGGAAGCTGCTGTCGACGGTTATGAACTGTTCAAGGACAA

CTTCCCAGCAGGTGAGAAGTTCGATAACGATGACACCAACGATCAATTCT

ACACGGTAATCTTCAAGCACCATCGTGAAAACGTTGATCCAAACCACTCC

TCGGCTGATGGCACGAAGGGTACGAAGACGCTGACGAAACGGTTCACTA

CAAGTACGCTAATGGCACCAAGGCGGCTGAAGATCAGACGGCTCAGGTAA

CGTTTACGCGGAACGGTGTCCTGGATGACGTTACGGGTATCGTGGCCTGG

GGCAAGTGGAACGAAGCCAGCCAGAGCTACAAGGCTTTGACTTCACCAAC

GATTGCCGGCTACGCGCCAAGCGAAGCGGTGGTAAAGCGCAGTTCCAACA

GCGATGCCGAACAAGGCCCAACGCTTACGGTCATCTACACGGCTGATGCC

TABLE 6-continued

Sequence of the MubBP(R5 + R6)-phy translational fusion. BamHI, SalI, PvuII and NheI cloning sites are in bold underlined (SEQ ID NO: 6). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is initalicized lowercase.

CAAAAGGTTCACGTTCAATACATTGATGGTGAAACTGACCAGATGCTGCG

TCAGGATGATTTGGACGGCTACACGGATGAAACGATTCCTTACAGCACGG

CTGAAGGCATCAAGAAGTTTGAAGGCGACGGTTATGAACTGTTCAAGGAC

AACTTCCCAGCAGGTGAGAAGTTCGATAACGATGACAAGAATGACCAAAC

CTACACGGTAATCTTCAAGCACCATCGTGAAAACGTTGATCCAAACCACT

CCTCGGCTGATGGCACGAAGGGTACGAAGACGCTGACGGAAACGGTTCAC

TACAAGTACGCAGATGGTACCAAGGCCGCTGAAGATCAGACGGCTCAGGT

AACGTTTACGCGGAACGGTGTCCTGGATGACGTTACGGGTATCGTGGCCT

GGGGCAAGTGGAACGAAGCCAGCCAGAGCTACAAGGCTTTGACTTCACCA

ACGATTGCCGGCTACACGCCAAGCGAAGCGGTGGTAAAGCGCAGTTCCAA

CAGCGATGCCGAACAAGGCCCAACGCTTACGGTCATCTACACGGCTGATG

CCCAAAAGGTTCACGTTCAATACATTGATGGTGAAACTGACCAGATGCTG

CGTCAGGATGATTTGGACGGCTACACGGATGAAACGATTCCTTACAGCAC

GGCTGAAGGCATCAAGAAGTTTGAAGGCGACGCAGCAGCTGCTGCCGCGG

CGGCAGCAGCAGAAGAACAAAACGGCATGAAGCTTGAACGCGTTGTCATT

*GTCAGCAGACACGGCGTTCGTGCGCCGACAAAATTCACACCGATTATGAA*

*GGATGTGACACCTGACCAATGGCCGCAATGGGATGTGCCGCTCGGCTGGC*

*TGACGCCAAGAGGCGGAGAGCTTGTTTCTGAGCTCGGACAATATCAGCGC*

*TTGTGGTTTACAAGCAAAGGTCTCCTGAATAACCAAACGTGCCCATCTCC*

*AGGACAAGTAGCTGTTATCGCTGACACTGATCAGCGGACAAGAAAAACAG*

*GCGAAGCATTTTTGGCAGGGCTTGCGCCGAAATGCCAAATTCAAGTACAC*

*TATCAAAAAGACGAAGAAAAAAACGACCCGCTGTTCAACCCGGTTAAAAT*

*GGGAAAATGCTCGTTTAACACTCTAAAGGTGAAGAATGCGATTTTAGAGC*

*GTGCCGGCGGAAACATTGAGCTTTACACACAGCGCTATCAATCATCTTTC*

*CGTACGCTTGAAAATGTGCTGAACTTCTCTCAATCTGAAACATGCAAAAC*

*AACAGAAAAATCAACAAAATGCACGCTTCCTGAAGCGCTGCCATCTGAGT*

*TTAAAGTAACGCCTGACAATGTATCCCTTCCTGGTGCATGGAGCCTTTCC*

*TCAACGCTGACTGAGATTTTCCTATTGCAGGAAGCTCAAGGCATGCCGCA*

*AGTCGCCTGGGGCCGGATTACCGGCGAAAAAGAGTGGAGGGATTTGCTGT*

*CACTTCACAACGCTCAATTTGACCTTCTTCAGCGTACACCAGAGGTTGCC*

*CGCTCCCGTGCAACCCCGCTTCTTGATATGATTGACACAGCTTTGCTGAC*

*AAATGGCACAACTGAAAACCGTTACGGCATCAAACTTCCGGTTTCTCTAT*

*TGTTTATTGCAGGGCATGACACAAACCTTGCCAACCTTTCCGGCGCGCTT*

*GATTTAAAATGGTCGCTGCCAGGACAGCCGGACAATACGCCGCCCGGCGG*

*AGAACTCGTATTTGAAAAATGGAAACGCACTTCTGACAACACTGACTGGG*

TABLE 6-continued

Sequence of the MubBP(R5 + R6)-phy translational fusion. BamHI, SalI, PvuII and NheI cloning sites are in bold underlined (SEQ ID NO: 6). Alanine spacer region is underlined uppercase. Codon-pair optimized phytase sequence is italicized uppercase. His-tag is in bold lowercase. Stop codons are in bold uppercase. Peptide signal is in underlined lowercase. Promoter is initalicized lowercase.

*TACAGGTTTCTTTCGTTTATCAAACGCTTCGTGACATGCGTGACATACAG*

*CCGCTCAGCCTTGAAAAGCCTGCCGGAAAAGTAGACTTAAAATTAATCGC*

*ATGTGAAGAGAAAAATTCTCAAGGTATGTGCTCGCTGAAATCATTCTCTC*

*GCTTGATTAAAGAAATCCGCGTGCCTGAATGTGCTGTCACAGAG*ctggtg ccgcgcggcagcagcagcggccaccaccaccaccaccacTAATAA<u>GCTAG</u>

<u>G</u>

Example 15

Design of Translational Fusion SpaB-Phy

This example describes the synthetic gene designed to over-express the fusion of the adhesion domain from SpaB of *Lactobacillus rhamnosus* GG to the amino-terminus of the *Citrobacter braakii* phytase.

From 5' to 3', the construction contains respectively (Table 7):
  the promoter region from *B. subtilis* amyQ
  the signal peptide from the *B. subtilis* ytwD gene (encoding the 32 first AA)
  *Lactobacillus rhamnosus* GG adhesion domain 177 AA between position 27 and position 203 in the sequence LGG_00443
  a ten Alanine spacer (including a PvuII restriction site)
  the codon-pair optimized *Citrobacter brakii* phytase gene appA deleted for its first 22 AA (signal peptide)
  a 56 bp sequence containing respectively a thrombine cleavage site, a hexahistidine tag, two successive stop codons and a NheI cleavage site.

TABLE 7

Sequence of the SpaB-phy translational fusion. BamHI, SalI, PvuII and NheI cloning sites are in bold underlined (SEQ ID NO: 7). Alanine spacer region is underlined lowercase italized case. Codon-pair optimized phytase sequence is italicized uppercase. His-tag is in bold lowercase. Stop codons are in bold uppercase. Peptide signal is in underlined lowercase. Promoter is in italicized lowercase.

*cggccgcccagactgtccgctgtgtaaaaaataggaataaagggggg*ttg ttattattttactgatatgtaaaatataatttgtataagaaaatgagagg gagaggaaattaattaaaaaaggagcgatttacatatgagttatgcagtt tgtagaatgcaaaaagtgaaatcagggGGATCCagaaaggaggtgatcca <u>atgaacacactggcaaactggaagaagtttttgcttgtggcggttatcat</u>

<u>ttgttttttggttccaattatgacaaaagcggagattgcggaagctgct</u>g

<u>tcgac</u>CAGCAGACACAGGCGGCAACTGTGCCGACCACTGTTGATGTTGTG

TTGCATAAGCTGTTGTTTAAAGATACCTTGCCAACTCAACAAGCAAATAA

TABLE 7-continued

Sequence of the SpaB-phy translational fusion. BamHI, SalI, PvuII and NheI cloning sites are in bold underlined (SEQ ID NO: 7). Alanine spacer region is underlined lowercase italized case. Codon-pair optimized phytase sequence is italicized uppercase. His-tag is in bold lowercase. Stop codons are in bold uppercase. Peptide signal is in underlined lowercase. Promoter is in italicized lowercase.

CGGGACAACAAAACCCGACTTTTCGCAGGCAGATGTGCCGTTAAACGGTG

TGACGTTCACAGTTTATGACGTGACCGCTGACTTTTGGCAGCTTGTCTCC

AAAAATGGCGGTGCGATTGAGGTAGCACAAACGACGTTGAGTCAAGATAG

CTATCAGCCTGCAAGCTCCAGCCTTATCGCACAGGTTGTGACGGCTGGTC

AGGGAGAAGCGTACTTTGGCGATTTACCACTCCGACAGGGGCAGCATGCT

GCGGTTTATCTTTTTAAAGAAACGGCGGCACCTAAGAATATTGAAGCCAG

TCAGAATCTTGTGGTTGTCATGTCAAGCAACCTTCAACATGGGAATCAAT

CACGCATTGATTTATTTCCTAAGAACAAAATGGTAAGTCGTCACACCGAT

GCCCCCAAAAAAGTTCCAAAGAAAATACGTCAATTG<u>CAGCAG</u>ct*gctgc*

*cgcggcggcagcagca*GAAGAACAAAACGGCATGAAGCTTGAACGCGTTG

TCATTGTCAGCAGACACGGCGTTCGTGCGCCGACAAAATTCACACCGATT

ATGAAGGATGTGACACCTGACCAATGGCCGCAATGGGATGTGCCGCTCGG

CTGGCTGACGCCAAGAGGCGGAGAGCTTGTTTCTGAGCTCGGACAATATC

AGCGCTTGTGGTTTACAAGCAAAGGTCTCCTGAATAACCAAACGTGCCCA

TCTCCAGGACAAGTAGCTGTTATCGCTGACACTGATCAGCGGACAAGAAA

AACAGGCGAAGCATTTTTGGCAGGGCTTGCGCCGAAATGCCAAATTCAAG

TACACTATCAAAAAGACGAAGAAAAAAACGACCCGCTGTTCAACCCGGTT

AAAATGGGAAAATGCTCGTTTAACACTCTAAAGGTGAAGAATGCGATTTT

AGAGCGTGCCGGCGGAAACATTGAGCTTTACACACAGCGCTATCAATCAT

CTTTCCGTACGCTTGAAAATGTGCTGAACTTCTCTCAATCTGAAACATGC

AAAACAACAGAAAAATCAACAAAATGCACGCTTCCTGAAGCGCTGCCATC

TGAGTTTAAAGTAACGCCTGACAATGTATCCCTTCCTGGTGCATGGAGCC

TTTCCTCAACGCTGACTGAGATTTTCCTATTGCAGGAAGCTCAAGGCATG

CCGCAAGTCGCCTGGGGCCGGATTACCGGCGAAAAAGAGTGGAGGGATTT

GCTGTCACTTCACAACGCTCAATTTGACCTTCTTCAGCGTACACCAGAGG

TTGCCCGCTCCCGTGCAACCCCGCTTCTTGATATGATTGACACAGCTTTG

CTGACAAATGGCACAACTGAAACCGTTACGGCATCAAACTTCCGGTTTC

TCTATTGTTTATTGCAGGGCATGACACAAACCTTGCCAACCTTTCCGGCG

CGCTTGATTTAAAATGGTCGCTGCCAGGACAGCCGGACAATACGCCGCCC

GGCGGAGAACTCGTATTTGAAAAATGGAAACGCACTTCTGACAACACTGA

CTGGGTACAGGTTTCTTTCGTTTATCAAACGCTTCGTGACATGCGTGACA

TACAGCCGCTCAGCCTTGAAAAGCCTGCCGGAAAAGTAGACTTAAAATTA

TABLE 7-continued

Sequence of the SpaB-phy translational fusion.
BamHI, SalI, PvuII and NheI cloning sites are
in bold underlined (SEQ ID NO: 7). Alanine spacer
region is underlined lowercase italized case.
Codon-pair optimized phytase sequence is
italicized uppercase. His-tag is in bold
lowercase. Stop codons are in bold uppercase.
Peptide signal is in underlined lowercase.
Promoter is in italicized lowercase.

*ATCGCATGTGAAGAGAAAAATTCTCAAGGTATGTGCTCGCTGAAATCATT*

*CTCTCGCTTGATTAAAGAAATCCGCGTGCCTGAATGTGCTGTCACAGAG*c tggtgccgcgcggcagcagcagcggccaccaccaccaccaccacTAATAA

GCTAGC

Example 16

Design of Translational Fusion Msa-Phy

This example describes the synthetic gene designed to over-express the fusion of the conA-like lectin domain of *Lactobacillus platarum* manose-specific adhesion Msa to the amino-terminus of the *Citrobacter braakii* phytase.

From 5' to 3', the construction contains respectively (Table 8):
- the promoter region from *B. subtilis* amyQ
- the signal peptide from the *B. subtilis* ytwD gene (encoding the 32 first AA)
- concavalin-like lectin domain from *Lactobacillus plantarum* Msa: 257 AA between position 263 and position 517 in the sequence EHS83650
- a ten Alanine spacer (including a PvuII restriction site)
- the codon-pair optimized *Citrobacter brakii* phytase gene appA deleted for its first 22 AA (signal peptide)
- a 56 bp sequence containing respectively a thrombin cleavage site, a hexahistidine tag, two successive stop codons and a NheI cleavage site.

TABLE 8

Sequence of the Msa-phy translational fusion.
BamHI, SalI, PvuII and NheI cloning sites
are in bold underlined (SEQ ID NO: 8). Alanine
spacer region is underlined lowercase italized
case. Codon-pair optimized phytase sequence is
italicized uppercase. His-tag is in bold
lowercase. Stop codons are in bold uppercase.
Peptide signal is in underlined lowercase.
Promoter is in italicized lowercase.

*cggccgcccagactgtccgctgtgtaaaaaataggaataaagggggg*ttg ttattattttactgatatgtaaaatataatttgtataagaaaatgagagg gagaggaaattaattaaaaaaggagcgatttacatatgagttatgcagtt tgtagaatgcaaaaagtgaaatcagggGGATCCAGAAAGGAGGTGATCCA

ATGAACACACTGGCAAACTGGAAGAAGTTTTTGCTTGTGGCGGTTATCAT

TTGTTTTTTGGTTCCAATTATGACAAAAGCGGAGATTGCGGAAGCTGCTG

TCGACTCTGATGAAGCGGCCTTGACTCATGTAGACAAGGACAATTTCCTA

AAGTATTTTAGTTTGAACGGATCTGCAACATATGATGCCAAGACGGGAAT

TGTAACTATTACGCCCAATCAAATAATCAAGTTGGTAATTTTTCATTAA

CCAGTAAGATTGATATGAATAAAAGCTTTACATTAACTGGTCAGGTAAAT

TABLE 8-continued

Sequence of the Msa-phy translational fusion.
BamHI, SalI, PvuII and NheI cloning sites
are in bold underlined (SEQ ID NO: 8). Alanine
spacer region is underlined lowercase italized
case. Codon-pair optimized phytase sequence is
italicized uppercase. His-tag is in bold
lowercase. Stop codons are in bold uppercase.
Peptide signal is in underlined lowercase.
Promoter is in italicized lowercase.

CTGGGGTCTAACCCGAATGGTGCGGATGGAATTGGGTTTGCTTTTCACAG

TGGCAATACAACTGACGTGGGAAATGCTGGTGGTAATTTAGGTATTGGTG

GATTGCAAGACGCTATCGGGTTCAAGCTAGACACATGGTTTAATAGCTAC

CAAGCACCATCATCAGATAAAAATGGGAGTGAAATCTCATCAACAAATTC

TAATGGCTTTGGTTGGAATGGTGACTCAGCCAACGCACCATATGGCACCT

TTGTCAAGACGAGTAACCAAGAAATTTCGACTGCGAATGGTTCTAAGGTA

CAGCGATGGTGGGCTCAAGATACAGGAGAGTCGCAGGCGTTAAGTAAAGC

GGATATTGATGGTAACTTTCATGATTTTGTAGTTAACTATGATGGTGCTA

CAAGAACGTTAACCGTTAGTTATACGCAAGCTAGTGGTAAAGTATTAACT

TGGAAGACGACTGTTGACAGTTCTTATCAAGCAATGGCCATGGTTGTCAG

TGCATCAACTGGTGCAGCTAAAAATTTACAACAATTTAAGTTGACTAGCT

TCGATTTTCAAGAAGCAGCGCAGCAGctgctgccgcggcggcagcagca

GAAGAACAAAACGGCATGAAGCTTGAACGCGTTGTCATTGTCAGCAGACA

CGGCGTTCGTGCGCCGACAAAATTCACACCGATTATGAAGGATGTGACAC

CTGACCAATGGCCGCAATGGGATGTGCCGCTCGGCTGGCTGACGCCAAGA

GGCGGAGAGCTTGTTTCTGAGCTCGGACAATATCAGCGCTTGTGGTTTAC

AAGCAAAGGTCTCCTGAATAACCAAACGTGCCCATCTCCAGGACAAGTAG

CTGTTATCGCTGACACTGATCAGCGGACAAGAAAAACAGGCGAAGCATTT

TTGGCAGGGCTTGCGCCGAAATGCCAAATTCAAGTACACTATCAAAAAGA

CGAAGAAAAAACGACCCGCTGTTCAACCCGGTTAAAATGGGAAAATGCT

CGTTTAACACTCTAAAGGTGAAGAATGCGATTTTAGAGCGTGCCGGCGGA

AACATTGAGCTTTACACACAGCGCTATCAATCATCTTTCCGTACGCTTGA

AAATGTGCTGAACTTCTCTCAATCTGAAACATGCAAAACAACAGAAAAAT

CAACAAAATGCACGCTTCCTGAAGCGCTGCCATCTGAGTTTAAAGTAACG

CCTGACAATGTATCCCTTCCTGGTGCATGGAGCCTTTCCTCAACGCTGAC

TGAGATTTTCCTATTGCAGGAAGCTCAAGGCATGCCGCAAGTCGCCTGGG

GCCGGATTACCGGCGAAAAAGAGTGGAGGGATTTGCTGTCACTTCACAAC

GCTCAATTTGACCTTCTTCAGCGTACACCAGAGGTTGCCCGCTCCCGTGC

AACCCCGCTTCTTGATATGATTGACACAGCTTTGCTGACAAATGGCACAA

CTGAAACCGTTACGGCATCAAACTTCCGGTTTCTCTATTGTTATTGCA

GGGCATGACACAAACCTTGCCAACCTTTCCGGCGCGCTTGATTTAAAATG

GTCGCTGCCAGGACAGCCGGACAATACGCCGCCCGGCGGAGAACTCGTAT

TTGAAAAATGGAAACGCACTTCTGACAACACTGACTGGGTACAGGTTTCT

TTCGTTTATCAAACGCTTCGTGACATGCGTGACATACAGCCGCTCAGCCT

TGAAAAGCCTGCCGGAAAAGTAGACTTAAAATTAATCGCATGTGAAGAGA

TABLE 8-continued

Sequence of the Msa-phy translational fusion. BamHI, SalI, PvuII and NheI cloning sites are in bold underlined (SEQ ID NO: 8). Alanine spacer region is underlined lowercase italized case. Codon-pair optimized phytase sequence is italicized uppercase. His-tag is in bold lowercase. Stop codons are in bold uppercase. Peptide signal is in underlined lowercase. Promoter is in italicized lowercase.

*AAAATTCTCAAGGTATGTGCTCGCTGAAATCATTCTCTCGCTTGATTAAA*

*GAAATCCGCGTGCCTGAATGTGCTGTCACAGAG*<u>*ctggtgccgcgcggcac*</u>

<u>*agcagcggc*</u>caccaccaccaccaccacTAATAA<u>GCTAGC</u>

Example 17

Design of Translational Fusion tasA BSP1-Phy

This example describes the gene sequence designed to over-express the fusion of a TasA protein of the undomesticated beneficial strain *B. subtilis* BSP1, to the amino-terminus of the *Citrobacter braakii* phytase.

From 5' to 3', the construction contains respectively (Table 9):
- the promoter region from *B. subtilis* amyQ
- the signal peptide from the *B. subtilis* ytwD gene (encoding the 32 first AA)
- *B. subtilis* BSP1 gene sequence encoding a 261 AA TasA protein (encoding a major component of biofilm matrix), deleted for its stop codon
- a ten Alanine spacer (including a PvuII restricton site)
- the codon-pair optimized *Citrobacter* brakii phytase gene appA deleted for its first 22 AA 15 (signal peptide)
- a 56 bp sequence containing respectively a thrombin cleavage site, a hexa-histidine tag, two successive stop codons and a NheI cleavage site.

TABLE 9

Sequence of the tasA_BSP1-phy translational fusion. BamHI, SalI, PvuII and NheI cloning sites are in bold underlined (SEQ ID NO: 9). Alanine spacer region is underlined uppercase. Codon-pair optimized phytase sequence is italicized uppercase. His-tag is in bold.

cggccgcccagactgtccgctgtgtaaaaaataggaataaaggggggttg ttattattttactgatatgtaaaatataatttgtataagaaaatgagagg gagaggaaattaattaaaaaaggagcgatttacatatgagttatgcagtt tgtagaatgcaaaaagtgaaatcagggGGATCCagaaaggaggtgatcca <u>atgaacacactggcaaactggaagaagttttttgcttgtggcggttatcat</u>

<u>ttgttttttggttccaattatgacaaaagcggagattgcggaagctgct</u>G

TCGACATGGGTATGAAAAAGAAATTGAGTTTAGGAGTTGCTTCTGCAGCA

CTAGGATTAGCTTTAGTTGGAGGAGGAACATGGGCAGCATTTAACGACAT

TAAATCAAAGGATGCTACTTTTGCATCAGGTACGCTTGATTTATCTGCTA

AAGAGAATTCAGCGAGTGTGAACTTATCAAATCTAAAGCCGGGAGATAAG

TTGACAAAGGATTTCCAATTTGAAAATAACGGATCACTTGCGATCAAAGA

AGTTCTAATGGCGCTTAATTATGGAGATTTTAAAGCAAACGGCGGCAGCA

TABLE 9-continued

Sequence of the tasA_BSP1-phy translational fusion. BamHI, SalI, PvuII and NheI cloning sites are in bold underlined (SEQ ID NO: 9). Alanine spacer region is underlined uppercase. Codon-pair optimized phytase sequence is italicized uppercase. His-tag is in bold.

ATACATCTCCAGAAGATTTCCTCAGCCAGTTTGAAGTGACATTGTTGACA

GTTGGAAAAGAGGGCGGCAATGGTTACCCGAAAAACATTATTTTAGATGA

TGCGAACCTTAAAGACTTGTATTTGATGTCTGCTAAAAATGATGCAGCGG

CTACTGAAAAAATCAAAAAACAAATTGACCCTAAATTCTTACATGCAAGC

GGTAAAGTCAATGTAGCAACAATTGACGGTAAAACTGCTCCTGAATATGA

TGGTGTTCCAAAAACACCAACTGACTTCGATCAGGTTCAAATGCAAATCC

AATTCAAAGATGATAAAACAAAAGATGAAAACGGGCTTATGGTTCAAAAT

AAATATCAAGGCAACTCCATTAAGCTTCAATTCTCGTTCGAAGCTACACA

GTGGAACGGCTTGACAATCAAAAAGGACCATACTGATAAAGACGGTTATG

TGAAAGAAAATGAAAAAGCGCACAGCGAGGATAAAAAT<u>GCAG</u>CAGCTGCT

GCTGCGGCTGCGGCAGCA*GAAGAACAAAACGGCATGAAGCTTGAACGCGT*

*TGTCATTGTCAGCAGACACGGCGTTCGTGCGCCGACAAAATTCACACCGA*

*TTATGAAGGATGTGACACCTGACCAATGGCCGCAATGGGATGTGCCGCTC*

*GGCTGGCTGACGCCAAGAGGCGGAGAGCTTGTTTCTGAGCTCGGACAATA*

*TCAGCGCTTGTGGTTTACAAGCAAAGGTCTCCTGAATAACCAAACGTGCC*

*CATCTCCAGGACAAGTAGCTGTTATCGCTGACACTGATCAGCGGACAAGA*

*AAAACAGGCGAAGCATTTTTGGCAGGGCTTGCGCCGAAATGCCAAATTCA*

*AGTACACTATCAAAAAGACGAAGAAAAAAACGACCCGCTGTTCAACCCGG*

*TTAAAATGGGAAAATGCTCGTTTAACACTCTAAAGGTGAAGAATGCGATT*

*TTAGAGCGTGCCGGCGGAAACATTGAGCTTTACACACAGCGCTATCAATC*

*ATCTTTCCGTACGCTTGAAAATGTGCTGAACTTCTCTCAATCTGAAACAT*

*GCAAAACAACAGAAAAATCAACAAAATGCACGCTTCCTGAAGCGCTGCCA*

*TCTGAGTTTAAAGTAACGCCTGACAATGTATCCCTTCCTGGTGCATGGAG*

*CCTTTCCTCAACGCTGACTGAGATTTTCCTATTGCAGGAAGCTCAAGGCA*

*TGCCGCAAGTCGCCTGGGGCCGGATTACCGGCGAAAAAGAGTGGAGGGAT*

*TTGCTGTCACTTCACAACGCTCAATTTGACCTTCTTCAGCGTACACCAGA*

*GGTTGCCCGCTCCCGTGCAACCCCGCTTCTTGATATGATTGACACAGCTT*

*TGCTGACAAATGGCACAACTGAAAACCGTTACGGCATCAAACTTCCGGTT*

*TCTCTATTGTTTATTGCAGGGCATGACACAAACCTTGCCAACCTTTCCGG*

*CGCGCTTGATTTAAAATGGTCGCTGCCAGGACAGCCGGACAATACGCCGC*

*CCGGCGGAGAACTCGTATTTGAAAAATGGAAACGCACTTCTGACAACACT*

*GACTGGGTACAGGTTTCTTTCGTTTATCAAACGCTTCGTGACATGCGTGA*

*CATACAGCCGCTCAGCCTTGAAAAGCCTGCCGGAAAAGTAGACTTAAAAT*

TABLE 9-continued

Sequence of the tasA_BSP1-phy translational
fusion. BamHI, SalI, PvuII and NheI cloning
sites are in bold underlined (SEQ ID NO: 9).
Alanine spacer region is underlined uppercase.
Codon-pair optimized phytase sequence is
italicized uppercase. His-tag is in bold.

TAATCGCATGTGAAGAGAAAAATTCTCAAGGTATGTGCTCGCTGAAATCA

TTCTCTCGCTTGATTAAAGAAATCCGCGTGCCTGAATGTGCTGTCACAGA

GCTGGTGCCGCGCGGCAGCAGCAGCGGCcaccaccaccaccaccacTAAT

AA<u>GCTAGC</u>

Example 18

Construction of B. subtilis Strain Expressing the Fusion tasA BSP1-Phy

This example describes the construction of B. subtilis strain BSP1-28 designed to overexpress the tasA_BSP1-phy fusion.

The tasA_BSP1 gene was amplified by PCR with a primer harboring SalI restriction site (5'-GCATGTCGACATGGG-TATGAAAAAGAAATTGAG (SEQ ID NO: 10)) and a primer harboring PvuII (5'-GCATCAGCTGCTGCATTTT-TATCCTCGCTGTGCGCTTTTTC (SEQ ID NO:11)). The resulting PCR product was double digested by SalI and PvuII restriction enzymes. After gel purification, the tas-A_BSP1 fragment was inserted into a multicopy plasmid (described in Example GS3) that has previously been double digested by SalI and PvuII restriction enzymes. The recombinant vector bearing tasA_BSP1-phy fusion was then transformed into B. subtilis 168 strain as known by people skilled in the art.

Example 19

Phytase Activity of Biofilm-Binding TasA BSP1-Phy Fusion

Figure 6:
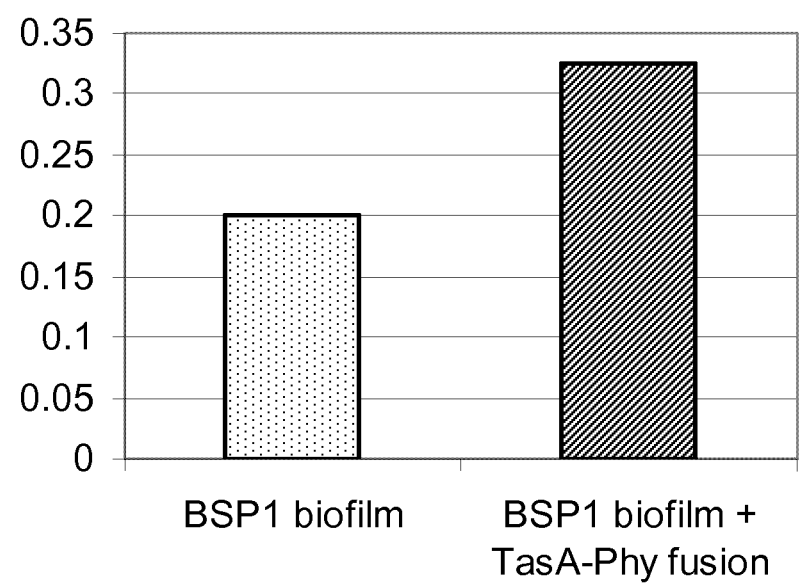

This example demonstrates that fusions bound to a bacterial biofilm exhibit significant phytase activity. FIG. 6 (Phytase activity of B. subtilis BSP1 biofilm supplemented with TasA_BSP1-Phy fusion protein) shows the histograms of phytase enzymatic activity bound to B. subtilis BSP1 biofilm. After washing, phytase activity of the biofilm-bound fusion was assessed as described in the "General methodology" section. The control prepared by omitting to mix the TasA_BSP1-Phy fusion protein to the preculture of Bacillus subtilis BSP1 biofilm former indicates the endogenous phytase activity of B. subtilis. The phytase activity assayed in the biofilm that has been incubated with the TasA_BSP1-Phy fusion protein (720 U/mg total protein) is significantly higher than the endogenous phytase activity of B. subtilis BSP1. This additional activity is due to the biofilm-bound phytase. One unit of phytase was defined as the amount of enzyme required to release 1 μmol of inorganic phosphate from sodium phytate in 1 min.

The invention claimed is:

1. A composition comprising a fusion protein, wherein the fusion protein comprises a protein comprising a *Lactobacillus* mucin binding domain linked to an enzyme, wherein the enzyme is selected from the group consisting of an enzyme having amylase activity, an enzyme having cellulase activity, an enzyme having galactanase activity, an enzyme having alpha-galactosidase activity, an enzyme having beta-glucanase activity, an enzyme having beta-glucuronidase activity, an enzyme having alkaline phosphatase activity, an enzyme having phospholipase activity, an enzyme having phytase activity, an enzyme having protease activity, and an enzyme having xylanase activity.

2. The composition of claim 1, wherein the enzyme is an enzyme having amylase activity.

3. The composition of claim 2, wherein the enzyme is an enzyme having alpha-amylase activity.

4. The composition of claim 1, wherein the enzyme is an enzyme having cellulase activity.

5. The composition of claim 1, wherein the enzyme is an enzyme having galactanase activity.

6. The composition of claim 1, wherein the enzyme is an enzyme having alpha-galactosidase activity.

7. The composition of claim 1, wherein the enzyme is an enzyme having beta-glucanase activity.

8. The composition of claim 1, wherein the enzyme is an enzyme having beta-glucuronidase activity.

9. The composition of claim 1, wherein the enzyme is an enzyme having alkaline phosphatase activity.

10. The composition of claim 1, wherein the enzyme is an enzyme having phospholipase activity.

11. The composition of claim 10, wherein the enzyme is a phospholipase A1, phospholipase A2, lysophospholipase, phospholipase C or phospholipase D.

12. The composition of claim 1, wherein the enzyme is an enzyme having phytase activity.

13. The composition of claim 12, wherein the phytase is a 3-phytase, 4-phytase, or 5-phytase.

14. The composition of claim 1, wherein the enzyme is an enzyme having protease activity.

15. The composition of claim 1, wherein the enzyme is an enzyme having xylanase activity.

16. The composition of claim 1, wherein the mucin binding domain is a conA-like lectin domain of *Lactobacillus platarum* manose-specific adhesion Msa.

17. The composition of claim 1, wherein the mucin binding domain is an adhesion domain from SpaB of *Lactobacillus rhamnosus* GG.

18. The composition of claim 1, wherein the mucin binding domain is a mucin binding domain of *Lactobacillus reuteri* 1063.

19. An animal feed composition comprising at least one composition of claim 1, and
   (a) at least one fat soluble vitamin;
   (b) at least one water soluble vitamin; and/or
   (c) at least one trace mineral.

20. A method for improving the nutritional value of an animal feed, comprising adding at least one composition of claim 1 to the feed.

21. A method of promoting feed utilization in animals comprising administering to the animal the composition of claim 1.

* * * * *